United States Patent
Herron et al.

(10) Patent No.: US 10,586,933 B2
(45) Date of Patent: Mar. 10, 2020

(54) ELECTROACTIVE METAL COMPLEXES

(71) Applicant: LG Chem, Ltd., Seoul (KR)

(72) Inventors: Norman Herron, Newark, DE (US); Adam Fennimore, Wilmington, DE (US)

(73) Assignee: LG Chem, Ltd. (KR)

( * ) Notice: Subject to any disclaimer, the term of this patent is extended or adjusted under 35 U.S.C. 154(b) by 188 days.

(21) Appl. No.: 15/113,501

(22) PCT Filed: Jan. 21, 2015

(86) PCT No.: PCT/US2015/012194
§ 371 (c)(1),
(2) Date: Jul. 22, 2016

(87) PCT Pub. No.: WO2015/112561
PCT Pub. Date: Jul. 30, 2015

(65) Prior Publication Data
US 2017/0012222 A1  Jan. 12, 2017

Related U.S. Application Data

(60) Provisional application No. 61/930,789, filed on Jan. 23, 2014.

(51) Int. Cl.
H01L 51/00 (2006.01)
C09K 11/06 (2006.01)
(Continued)

(52) U.S. Cl.
CPC ...... H01L 51/0085 (2013.01); C07F 15/0033 (2013.01); C09K 11/025 (2013.01);
(Continued)

(58) Field of Classification Search
CPC combination set(s) only.
See application file for complete search history.

(56) References Cited

U.S. PATENT DOCUMENTS 6,670,645 B2   12/2003   Grushin et al.
6,875,524 B2    4/2005   Hatwar et al.
(Continued)

FOREIGN PATENT DOCUMENTS

KR   10-2009-0073850 A   7/2009
WO      2003/008424 A1   1/2003
(Continued)

OTHER PUBLICATIONS

Wang, Y., Kirk-Othmer Encyclopedia of Chemical Technology, Fourth Edition, 1996, vol. 18, pp. 837-860 (Book Not Included).
(Continued)

*Primary Examiner* — Jennifer A Chriss
*Assistant Examiner* — Sean M DeGuire
(74) *Attorney, Agent, or Firm* — Lerner, David, Littenberg, Krumholz & Mentlik, LLP

(57) ABSTRACT

Disclosed is a compound having Formula I

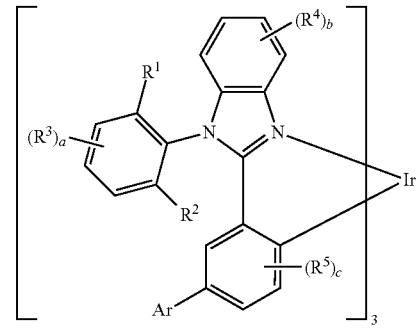

Formula I

In Formula I: Ar is aryl or deuterated aryl; $R^1$ and $R^2$ are the same or different and can be alkyl, silyl, aryl, deuterated
(Continued)

alkyl, deuterated silyl, or deuterated aryl; $R^3$-$R^5$ are the same or different at each occurrence and can be D, alkyl, silyl, aryl, deuterated alkyl, deuterated aryl, or deuterated silyl; where two adjacent $R^4$ groups can be joined together to form a fused 6-membered aromatic or deuterated aromatic ring; a and c are independently an integer from 0-3; and b is an integer from 0-4.

Formula I may exist as either fac or mer structural isomers including mixtures of both.

18 Claims, 5 Drawing Sheets

(51) Int. Cl.
  *C07F 15/00* (2006.01)
  *C09K 11/02* (2006.01)
  *H01L 51/50* (2006.01)
(52) U.S. Cl.
  CPC .......... *C09K 11/06* (2013.01); *H01L 51/0072* (2013.01); *C09K 2211/1007* (2013.01); *C09K 2211/1044* (2013.01); *C09K 2211/185* (2013.01); *H01L 51/5016* (2013.01)

(56) References Cited

U.S. PATENT DOCUMENTS

| 2004/0102577 | A1 | 5/2004 | Hsu et al. |
| 2004/0127637 | A1 | 7/2004 | Hsu et al. |
| 2005/0158577 | A1 | 7/2005 | Ishibashi et al. |
| 2005/0205860 | A1 | 9/2005 | Hsu et al. |

FOREIGN PATENT DOCUMENTS

| WO | 2003/040257 | A1 | 5/2003 | |
| WO | 2003/063555 | A1 | 7/2003 | |
| WO | 2003/091688 | A2 | 11/2003 | |
| WO | 2004/016710 | A1 | 2/2004 | |
| WO | 2009/018009 | A1 | 2/2009 | |
| WO | WO-2010004877 | A1 * | 1/2010 | ............. C09K 11/06 |
| WO | 2010/129323 | A1 | 11/2010 | |

OTHER PUBLICATIONS

Shan, Guo-Gang et al., "Enhancing the luminescence properties and stability of cationiciridium(III) complexes based on phenylbenzoimidazole ligand: a combined experimental and theoretical study," Dalton Trans., 2013, vol. 32, Issue 31, pp. 11056-11065.

PCT International Search Report for Application No. PCT/US2015/012194; Lee Younjoo, Authorized Officer; ISA/KR; May 1, 2015.

Jiang, H. J. ,"Organic Ambipolar Conjugated Molecules for Electronics: Synthesis and Structure—Property Relationships," Macromolecular Rapid Communications, 2010, vol. 31, pp. 2007-2034.

Gustafsson, G. et al. "Flexible light-emitting diodes made from soluble conducting polymers," Letters to Nature, Jun. 11, 1992, vol. 357, pp. 477-479.

CRC Handbook of Chemistry and Physics, 81st Edition, 2000-2001 (Book Not Included).

* cited by examiner

US 10,586,933 B2

ELECTROACTIVE METAL COMPLEXES

BACKGROUND INFORMATION

Field of the Disclosure

This disclosure relates in general to electroactive metal complexes and their use in electronic devices.

Background

Organic electronic devices that emit light, such as light-emitting diodes that make up displays, are present in many different kinds of electronic equipment. In all such devices, an organic active layer is sandwiched between two electrical contact layers. At least one of the electrical contact layers is light-transmitting so that light can pass through the electrical contact layer. The organic active layer emits light through the light-transmitting electrical contact layer upon application of electricity across the electrical contact layers.

It is well known to use electroactive complexes as the active component in light-emitting diodes. Some organic molecules, such as anthracene, thiadiazole derivatives, and coumarin derivatives are known to show electroluminescence. Certain metal complexes, particularly iridium and platinum complexes, are also known to show electroluminescence. In some cases these metal complexes are present as a dopant in a host material to improve processing and/or electronic properties.

There is a continuing need for new luminescent materials.

SUMMARY

Disclosed is a compound having Formula I

Formula I

[structure showing benzimidazole-based ligand with substituents $R^1$, $R^2$, $(R^3)_a$, $(R^4)_b$, $(R^5)_c$, Ar, coordinated to Ir, with subscript 3]

wherein:
  Ar is aryl or deuterated aryl;
  $R^1$ and $R^2$ are the same or different and are selected from the group including only alkyl, silyl, aryl, deuterated alkyl, deuterated silyl, and deuterated aryl;
  $R^3$-$R^5$ are the same or different at each occurrence and are selected from the group including only D, alkyl, silyl, aryl, deuterated alkyl, deuterated aryl, and deuterated silyl; where two adjacent $R^4$ groups can be joined together to form a fused 6-membered aromatic or deuterated aromatic ring;
  a and c are independently an integer from 0-3; and
  b is an integer from 0-4;
wherein:
  Formula I may exist as either fac or mer structural isomers including mixtures of both.

There is also provided an organic electronic device including a first electrical contact, a second electrical contact and a photoactive layer therebetween, the photoactive layer including the material having Formula I.

The foregoing general description and the following detailed description are exemplary and explanatory only and are not restrictive of the invention, as defined in the appended claims.

BRIEF DESCRIPTION OF THE DRAWINGS

Embodiments are illustrated in the accompanying figures to improve understanding of concepts as presented herein.

Figure 1:
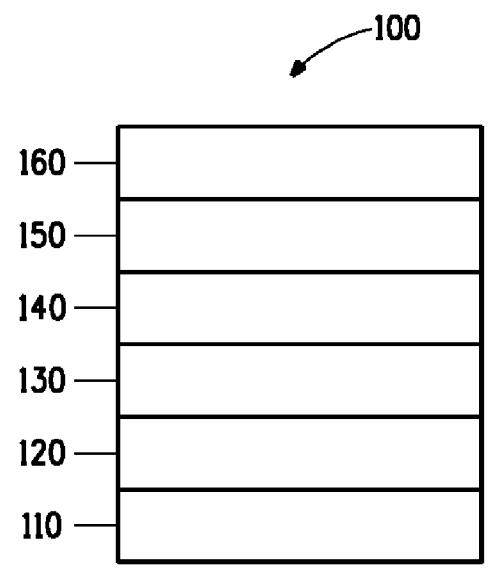
FIG. 1 includes an illustration of an organic light-emitting device.

Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

Many aspects and embodiments are described herein and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims. The detailed description first addresses Definitions and Clarification of Terms followed by the Material Having Formula I, Synthesis, Devices, and finally Examples.

1. Definitions and Clarification of Terms

Before addressing details of embodiments described below, some terms are defined or clarified.

The term "alkoxy" is intended to mean a group having the formula —OR, which is attached via the oxygen, where R is an alkyl.

The term "alkyl" is intended to mean a group derived from an aliphatic hydrocarbon and includes a linear, a branched, or a cyclic group. In some embodiments, an alkyl has from 1-20 carbon atoms.

The term "aryl" is intended to mean a group derived from an aromatic compound. The term "aromatic compound" is intended to mean an organic compound including at least one unsaturated cyclic group having delocalized pi electrons. The term is intended to encompass both hydrocarbon aromatic compounds having only carbon and hydrogen atoms, and heteroaromatic compounds wherein one or more of the carbon atoms within the cyclic group has been replaced by another atom, such as nitrogen, oxygen, sulfur, or the like. In some embodiments, hydrocarbon aryl groups have 6-60 ring carbons. In some embodiments, heterocyclic aryl groups have 3-60 ring carbons.

The term "charge transport," when referring to a layer, material, member, or structure is intended to mean such layer, material, member, or structure facilitates migration of such charge through the thickness of such layer, material, member, or structure with relative efficiency and small loss of charge. Hole transport materials facilitate positive charge; electron transport materials facilitate negative charge. Although light-emitting materials may also have some charge transport properties, the term "charge transport layer, material, member, or structure" is not intended to include a layer, material, member, or structure whose primary function is light emission.

The term "deuterated" or "deuterated analog" is intended to mean that at least one hydrogen ("H") has been replaced by deuterium ("D"). The term "deuterated analog" refers to a structural analog of a compound or group in which one or more available hydrogens have been replaced with deuterium. In a deuterated compound or deuterated analog, the deuterium is present in at least 100 times the natural abundance level.

The term "dopant" is intended to mean a material, within a layer including a host material, that changes the electronic characteristic(s) or the targeted wavelength(s) of radiation emission, reception, or filtering of the layer compared to the electronic characteristic(s) or the wavelength(s) of radiation emission, reception, or filtering of the layer in the absence of such material.

The term "electroactive" when referring to a layer or material, is intended to mean a layer or material that exhibits electronic or electro-radiative properties. In an electronic device, an electroactive material electronically facilitates the operation of the device. Examples of electroactive materials include, but are not limited to, materials which conduct, inject, transport, or block a charge, where the charge can be either an electron or a hole, and materials which emit radiation or exhibit a change in concentration of electron-hole pairs when receiving radiation. Examples of inactive materials include, but are not limited to, insulating materials and environmental barrier materials.

The term "electron-trap" or "electron-trap material" is intended to mean a compound that possesses a lowest unoccupied molecular orbital (LUMO) lying further in energy from the vacuum level than the LUMO of any other material present in the layer in which it is embedded. As such, it is the preferred site for negative charge to reside in that layer and if the trap material is present below the percolation volume (<~15%) such negative charge becomes localized upon molecules of the trap material presenting a hindrance to negative charge mobility within that layer.

The term "fac" is intended to mean a type of coordination about an octahedral metal center where each set of three bidentate N—C ligands have the coordinated N atoms lying on one face of the octahedron surrounding the metal atom so that any two of the three coordinated N atoms are mutually cis.

The term "fluorescent" as it refers to a material, is intended to mean a material which emits light from an excited state having substantially all singlet character.

The prefix "hetero" indicates that one or more carbon atoms have been replaced with a different atom. In some embodiments, the different atom is N, O, or S.

The term "hole-trap" or "hole-trap material" is intended to mean a compound that possesses a highest occupied molecular orbital (HOMO) lying closer in energy to the vacuum level than the HOMO of any other material present in the layer in which it is embedded. As such, it is the preferred site for positive charge to reside in that layer and, if the trap material is present below the percolation volume (<~15%), such positive charge becomes localized upon molecules of the trap material presenting a hindrance to positive charge mobility within that layer.

The term "host material" is intended to mean a material, usually in the form of a layer, to which a dopant may be added. The host material may or may not have electronic characteristic(s) or the ability to emit, receive, or filter radiation.

The terms "luminescent material" and "emitter" are intended to mean a material that emits light when activated by an applied voltage (such as in a light-emitting diode or light-emitting electrochemical cell). The term "green luminescent material" is intended to mean a material capable of emitting radiation that has an emission maximum at a wavelength in a range of approximately 495-569 nm. The term "orange luminescent material" is intended to mean a material capable of emitting radiation that has an emission maximum at a wavelength in a range of approximately 590-619 nm. The term "red luminescent material" is intended to mean a material capable of emitting radiation that has an emission maximum at a wavelength in a range of approximately 620-750 nm. The term "yellow luminescent material" is intended to mean a material capable of emitting radiation that has an emission maximum at a wavelength in a range of approximately 570-589 nm.

The term "layer" is used interchangeably with the term "film" and refers to a coating covering a desired area. The term is not limited by size. The area can be as large as an entire device or as small as a specific functional area such as the actual visual display, or as small as a single sub-pixel. Layers and films can be formed by any conventional deposition technique, including vapor deposition, liquid deposition (continuous and discontinuous techniques), and thermal transfer. Continuous deposition techniques, include but are not limited to, spin coating, gravure coating, curtain coating, dip coating, slot-die coating, spray coating, and continuous nozzle coating or printing. Discontinuous deposition techniques include, but are not limited to, ink jet printing, gravure printing, and screen printing.

The term "mer" is intended to mean a type of coordination about an octahedral metal center where each set of three bidentate N—C ligands have the N atoms coordinated in a plane passing through the metal atom.

The term "organic electronic device" or sometimes just "electronic device" is intended to mean a device including one or more organic semiconductor layers or materials.

The term "phosphorescent" as it refers to a material, is intended to mean a material which emits light from an excited state having significant triplet character.

The term "photoactive" refers to a material or layer that emits light when activated by an applied voltage (such as in a light emitting diode or chemical cell) or responds to radiant energy and generates a signal with or without an applied bias voltage (such as in a photodetector or a photovoltaic cell).

The term "siloxane" refers to the group $R_3SiO$—, where R is H, D, C1-20 alkyl, fluoroalkyl, or aryl. In some embodiments, one or more carbons in an R alkyl group are replaced with Si.

The term "silyl" refers to the group $R_3Si$—, where R is H, D, C1-20 alkyl, fluoroalkyl, or aryl. In some embodiments, one or more carbons in an R alkyl group are replaced with Si.

All groups may be unsubstituted or substituted. In some embodiments, the substituents are selected from the group including only deuterium ("D"), halide, alkyl, alkoxy, aryl, aryloxy, silyl, siloxane, alkylamino, arylamino, and cyano.

In this specification, unless explicitly stated otherwise or indicated to the contrary by the context of usage, where an embodiment of the subject matter hereof is stated or described as comprising, including, containing, having, being composed of or being constituted by or of certain features or elements, one or more features or elements in addition to those explicitly stated or described may be present in the embodiment. An alternative embodiment of the disclosed subject matter hereof is described as consisting essentially of certain features or elements, in which embodiment features or elements that would materially alter the principle of operation or the distinguishing characteristics of the embodiment are not present therein. A further alternative embodiment of the described subject matter hereof is described as consisting of certain features or elements, in which embodiment, or in insubstantial variations thereof, only the features or elements specifically stated or described are present.

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Group numbers corresponding to columns within the Periodic Table of the elements use the "New Notation" convention as seen in the *CRC Handbook of Chemistry and Physics*, 81$^{st}$ Edition (2000-2001).

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

To the extent not described herein, many details regarding specific materials, processing acts, and circuits are conventional and may be found in textbooks and other sources within the organic light-emitting diode display, photodetector, photovoltaic, and semiconductive member arts.

2. Materials Having Formula I

The new materials described herein have Formula I

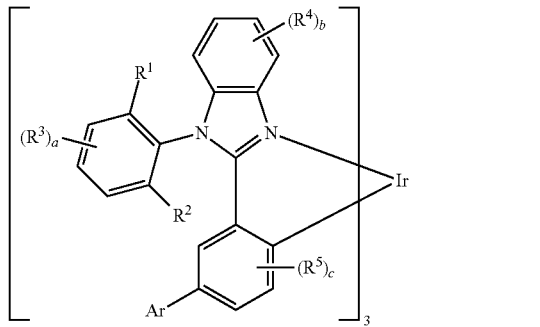

Formula I wherein:
Ar is aryl or deuterated aryl;
R$^1$ and R$^2$ are the same or different and are selected from the group including only alkyl, silyl, aryl, deuterated alkyl, deuterated silyl, and deuterated aryl;
R$^3$-R$^5$ are the same or different at each occurrence and are selected from the group including only D, alkyl, silyl, aryl, deuterated alkyl, deuterated aryl, and deuterated silyl; where two adjacent R$^4$ groups can be joined together to form a fused 6-membered aromatic or deuterated aromatic ring;
a and c are independently an integer from 0-3; and
b is an integer from 0-4.

The compound of Formula I may exist as either fac or mer structural isomers or as mixtures of both.

In some embodiments, the compounds having Formula I are useful as emissive materials. In some embodiments, the compounds are green emissive materials. In some embodiments, the compounds are red emissive materials.

In some embodiments, the compounds having Formula I are used alone as emissive materials.

In some embodiments, the compounds having Formula I are used as an emissive dopant in a host material.

In some embodiments, the compounds having Formula I are used as electron-trap materials.

In some embodiments, the compounds having Formula I are used as hole-trap materials.

In some embodiments, compounds having Formula I have an unexpectedly narrower emission profile compared to prior art compounds having a benzimidazole ligand. In some embodiments, the emission profile has a width at half the maximum intensity ("FWHM") that is less than 60 nm; in some embodiments less than 50 nm. This is advantageous for display devices for producing more saturated color.

Unexpectedly, in some embodiments, devices using compounds having Formula I have higher efficiency compared to devices using prior art compounds. This is advantageous for display devices and lighting devices for reducing energy consumption.

Unexpectedly, in some embodiments, devices using compounds having Formula I have longer lifetimes compared to devices using prior art compounds. This is advantageous for display and lighting applications.

Unexpectedly, in some embodiments, devices using the compounds having Formula I have simultaneous narrower emission profiles, higher efficiency, and longer lifetimes compared to devices using prior art compounds. This is advantageous for overall performance of display devices and lighting devices.

In some embodiments of Formula I, Ar is selected from the group including only phenyl, 3-biphenyl, 4-biphenyl, 4,4'-terphenyl, 4,3'-terphenyl, 3,4'-terphenyl, 3,3'-terphenyl, 3,5'-terphenyl, 1-naphthyl, 2-naphthyl, 4-(1-naphthyl)phenyl, 4-(2-naphthyl)phenyl, 3-(1-naphthyl)phenyl, 3-(2-naphthyl)phenyl, substituted phenyl, substituted 3-biphenyl, substituted 4-biphenyl, substituted 4,4'-terphenyl, substituted 4,3'-terphenyl, substituted 3,4'-terphenyl, substituted 3,3'-terphenyl, substituted 3,5'-terphenyl, substituted 1-naphthyl, substituted 2-naphthyl, substituted 4-(1-naphthyl)phenyl, substituted 4-(2-naphthyl)phenyl, substituted 3-(1-naphthyl)phenyl, substituted 3-(2-naphthyl)phenyl, and deuterated analogs thereof.

In some embodiments of Formula I, R$^1$ is selected from the group including only linear alkyl having 1-10 carbons, branched alkyl having 3-10 carbons, cycloalkyl having 6-12 ring carbons, silyl, and deuterated analogs thereof.

In some embodiments of Formula I, $R^1$ is selected from the group including only phenyl, naphthyl, biphenyl, terphenyl, substituted derivatives thereof, and deuterated analogs thereof.

In some embodiments of Formula I, $R^2$ is selected from the group including only linear alkyl having 1-10 carbons, branched alkyl having 3-10 carbons, cycloalkyl having 6-12 ring carbons, silyl, and deuterated analogs thereof.

In some embodiments of Formula I, $R^2$ is selected from the group including only phenyl, naphthyl, biphenyl, terphenyl, substituted derivatives thereof, and deuterated analogs thereof.

In some embodiments of Formula I, a=0.

In some embodiments of Formula I, a=1.

In some embodiments of Formula I, a>0 and $R^3$ is selected from the group including only D, alkyl having 1-10 carbons, and deuterated alkyl having 1-10 carbons.

In some embodiments of Formula I, b=0.

In some embodiments of Formula I, b=1 or 2.

In some embodiments of Formula I, b>0 and $R^4$ is selected from the group including only D, alkyl having 1-10 carbons, and deuterated alkyl having 1-10 carbons.

In some embodiments of Formula I, c=0.

In some embodiments of Formula I, c=1 or 2.

In some embodiments of Formula I, c>0 and $R^5$ is selected from the group including only D, alkyl having 1-10 carbons, and deuterated alkyl having 1-10 carbons.

In some embodiments, the compounds having Formula I are green emissive materials and the green emission has color coordinates of x=0.20-0.35, and y=0.55-0.72, according to the C.I.E. chromaticity scale (Commision Internationale de L'Eclairage, 1931).

In some embodiments, the compounds have Formula II

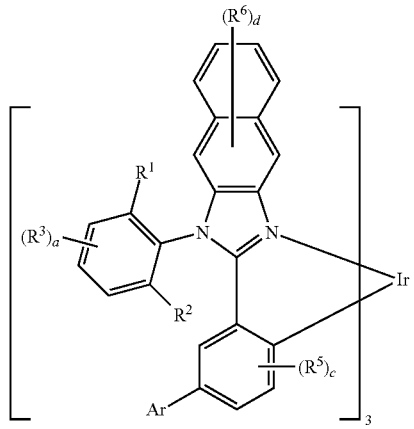

Formula II wherein:
Ar is aryl or deuterated aryl;
$R^1$ and $R^2$ are the same or different and are selected from the group including only alkyl, silyl, aryl, deuterated alkyl, deuterated silyl, and deuterated aryl;
$R^3$, $R^5$ and $R^6$ are the same or different at each occurrence and are selected from the group including only D, alkyl, silyl, aryl, deuterated alkyl, deuterated aryl, and deuterated silyl;
a and c are independently an integer from 0-3; and
d is an integer from 0-6.

The compound of Formula II may exist as either fac or mer structural isomers or as mixtures of both.

In some embodiments of Formula II, Ar is selected from the group including only phenyl, 3-biphenyl, 4-biphenyl, 4,4'-terphenyl, 4,3'-terphenyl, 3,4'-terphenyl, 3,3'-terphenyl, 3,5'-terphenyl, 1-naphthyl, 2-naphthyl, 4-(1-naphthyl)phenyl, 4-(2-naphthyl)phenyl, 3-(1-naphthyl)phenyl, 3-(2-naphthyl)phenyl, substituted phenyl, substituted 3-biphenyl, substituted 4-biphenyl, substituted 4,4'-terphenyl, substituted 4,3'-terphenyl, substituted 3,4'-terphenyl, substituted 3,3'-terphenyl, substituted 3,5'-terphenyl, substituted 1-naphthyl, substituted 2-naphthyl, substituted 4-(1-naphthyl)phenyl, substituted 4-(2-naphthyl)phenyl, substituted 3-(1-naphthyl)phenyl, substituted 3-(2-naphthyl)phenyl, and deuterated analogs thereof.

In some embodiments of Formula II, $R^1$ is selected from the group including only linear alkyl having 1-10 carbons, branched alkyl having 3-10 carbons, cycloalkyl having 6-12 ring carbons, silyl, and deuterated analogs thereof.

In some embodiments of Formula II, $R^1$ is selected from the group including only phenyl, naphthyl, biphenyl, terphenyl, substituted derivatives thereof, and deuterated analogs thereof.

In some embodiments of Formula II, $R^2$ is selected from the group including only linear alkyl having 1-10 carbons, branched alkyl having 3-10 carbons, cycloalkyl having 6-12 ring carbons, silyl, and deuterated analogs thereof.

In some embodiments of Formula II, $R^2$ is selected from the group including only phenyl, naphthyl, biphenyl, terphenyl, substituted derivatives thereof, and deuterated analogs thereof.

In some embodiments of Formula II, a=0.

In some embodiments of Formula II, a=1.

In some embodiments of Formula II, a>0 and $R^3$ is selected from the group including only D, alkyl having 1-10 carbons, and deuterated alkyl having 1-10 carbons.

In some embodiments of Formula II, c=0.

In some embodiments of Formula II, c=1 or 2.

In some embodiments of Formula II, c>0 and $R^5$ is selected from the group including only D, alkyl having 1-10 carbons, and deuterated alkyl having 1-10 carbons.

In some embodiments of Formula II, d=0.

In some embodiments of Formula II, d=1 or 2.

In some embodiments of Formula II, b>0 and $R^6$ is selected from the group including only D, alkyl having 1-10 carbons, and deuterated alkyl having 1-10 carbons.

In some embodiments, the compounds having Formula II are orange or red emissive materials, and the emission has color coordinates of x=0.55-0.70, and y=0.30-0.4, according to the C.I.E. chromaticity scale (Commision Internationale de L'Eclairage, 1931).

Some additional, non-limiting embodiments of Formula I and Formula II are given below.

Embodiment 1

The compound of Formula I or Formula II, wherein the compound is deuterated.

Embodiment 2

The compound of Formula I or Formula II, wherein the compound is at least 10% deuterated. By "% deuterated" or "% deuteration" is meant the ratio of deuterons to the total of hydrogens plus deuterons, expressed as a percentage. The deuteriums may be on the same or different groups.

Embodiment 3

The compound of Formula I or Formula II, wherein the compound is at least 20% deuterated.

Embodiment 4

The compound of Formula I or Formula II wherein the compound is at least 30% deuterated.

Embodiment 5

The compound of Formula I or Formula II, wherein the compound is at least 40% deuterated.

Embodiment 6

The compound of Formula I or Formula II, wherein the compound is at least 50% deuterated.

Embodiment 7

The compound of Formula I or Formula II, wherein the compound is at least 60% deuterated.

Embodiment 8

The compound of Formula I or Formula II, wherein the compound is at least 70% deuterated.

Embodiment 9

The compound of Formula I or Formula II, wherein the compound is at least 80% deuterated.

Embodiment 10

The compound of Formula I or Formula II, wherein the compound is at least 90% deuterated.

Embodiment 11

The compound of Formula I or Formula II, wherein the compound is greater than 95% deuterated.

Embodiment 12

The compound of Formula I or Formula II, wherein Ar is phenyl.

Embodiment 13

The compound of Formula I or Formula II, wherein, Ar is 3-biphenyl.

Embodiment 14

The compound of Formula I or Formula II, wherein Ar is 4-biphenyl.

Embodiment 15

The compound of Formula I or Formula II, wherein Ar is 4,4'-terphenyl.

Embodiment 16

The compound of Formula I or Formula II, wherein Ar is 4,3'-terphenyl.

Embodiment 17

The compound of Formula I or Formula II, wherein Ar is 3,4'-terphenyl.

Embodiment 18

The compound of Formula I or Formula II, wherein Ar is 3,3'-terphenyl.

Embodiment 19

The compound of Formula I or Formula II, wherein Ar is 3,5'-terphenyl.

Embodiment 20

The compound of Formula I or Formula II, wherein Ar is 1-naphthyl.

Embodiment 21

The compound of Formula I or Formula II, wherein Ar is 2-naphthyl.

Embodiment 22

The compound of Formula I or Formula II, wherein Ar is 4-(1-naphthyl)phenyl.

Embodiment 23

The compound of Formula I or Formula II, wherein Ar is 4-(2-naphthyl)phenyl.

Embodiment 24

The compound of Formula I or Formula II, wherein Ar is 3-(1-naphthyl)phenyl.

Embodiment 25

The compound of Formula I or Formula II, wherein Ar is 3-(2-naphthyl)phenyl.

Embodiment 26

The compound of Formula I or Formula II, wherein Ar has at least one substituent.

Embodiment 27

The compound of any of Embodiments 12-25, wherein Ar has at least one substituent.

Embodiment 28

The compound of Embodiment 26 or 27, wherein the substituent is D.

Embodiment 29

The compound of Embodiment 26 or 27, wherein the substituent is an alkyl group having 1-20 carbons.

Embodiment 30

The compound of Embodiment 26 or 27, wherein the substituent is a silyl group.

Embodiment 31

The compound of Embodiment 29 or 30, wherein the substituent is deuterated.

Embodiment 32

The compound of Formula I or Formula II, wherein $R^1$ is a linear alkyl group having 1-10 carbons.

Embodiment 33

The compound of Formula I or Formula II, wherein $R^1$ is a deuterated linear alkyl group having 1-10 carbons.

Embodiment 34

The compound of Formula I or Formula II, wherein $R^1$ is a branched alkyl group having 3-10 carbons.

Embodiment 35

The compound of Formula I or Formula II, wherein $R^1$ is a deuterated branched alkyl group having 3-10 carbons.

Embodiment 36

The compound of Formula I or Formula II, wherein $R^1$ is a cycloalkyl group having 6-12 ring carbons.

Embodiment 37

The compound of Formula I or Formula II, wherein $R^1$ is a deuterated cycloalkyl group having 6-12 ring carbons.

Embodiment 38

The compound of Formula I or Formula II, wherein $R^1$ is a silyl group having the formula $R_3Si-$, where R is the same or different at each occurrence and is an alkyl group having 1-12 carbons.

Embodiment 39

The compound of Formula I or Formula II, wherein $R^1$ is a deuterated silyl group having the formula $R_3Si-$, where R is the same or different at each occurrence and is a deuterated alkyl group having 1-12 carbons.

Embodiment 40

The compound of Formula I or Formula II, wherein $R^1$ is an aryl group.

Embodiment 41

The compound of Formula I or Formula II, wherein $R^1$ is phenyl.

Embodiment 42

The compound of Formula I or Formula II, wherein $R^1$ is naphthyl.

Embodiment 43

The compound of Formula I or Formula II, wherein $R^1$ is biphenyl

Embodiment 44

The compound of Formula I or Formula II, wherein $R^1$ is terphenyl.

Embodiment 45

The compound of any of Embodiments 40-44, wherein $R^1$ has at least one substituent.

Embodiment 46

The compound of any of Embodiments 40-45, wherein $R^1$ is deuterated.

Embodiment 47

The compound of Formula I or Formula II, wherein $R^1$ is a linear alkyl group having 1-10 carbons.

Embodiment 48

The compound of Formula I or Formula II, wherein $R^2$ is a deuterated linear alkyl group having 1-10 carbons.

Embodiment 49

The compound of Formula I or Formula II, wherein $R^2$ is a branched alkyl group having 3-10 carbons.

Embodiment 50

The compound of Formula I or Formula II, wherein $R^2$ is a deuterated branched alkyl group having 3-10 carbons.

Embodiment 51

The compound of Formula I or Formula II, wherein $R^2$ is a cycloalkyl group having 6-12 ring carbons.

Embodiment 52

The compound of Formula I or Formula II, wherein $R^2$ is a deuterated cycloalkyl group having 6-12 ring carbons.

Embodiment 53

The compound of Formula I or Formula II, wherein $R^2$ is a silyl group having the formula $R_3Si-$, where R is the same or different at each occurrence and is an alkyl group having 1-12 carbons.

Embodiment 54

The compound of Formula I or Formula II, wherein $R^2$ is a deuterated silyl group having the formula $R_3Si-$, where R is the same or different at each occurrence and is a deuterated alkyl group having 1-12 carbons.

Embodiment 55

The compound of Formula I or Formula II, wherein $R^2$ is an aryl group.

Embodiment 56

The compound of Formula I or Formula II, wherein $R^2$ is phenyl.

Embodiment 57

The compound of Formula I or Formula II, wherein $R^2$ is naphthyl.

Embodiment 58

The compound of Formula I or Formula II, wherein $R^2$ is biphenyl

Embodiment 59

The compound of Formula I or Formula II, wherein $R^2$ is terphenyl.

Embodiment 60

The compound of any of Embodiments 40-44, wherein $R^2$ has at least one substituent.

Embodiment 61

The compound of any of Embodiments 40-45, wherein $R^2$ is deuterated.

Embodiment 62

The compound of Formula I or Formula II, wherein $R^3$ is D.

Embodiment 63

The compound of Formula I, wherein $R^4$ is D.

Embodiment 64

The compound of Formula I or Formula II, wherein $R^5$ is D.

Embodiment 65

The compound of Formula II, wherein $R^6$ is D.

Embodiment 66

The compound of Formula I or Formula II, wherein $R^3$ is an alkyl group having 1-10 carbons.

Embodiment 67

The compound of Formula I or Formula II, wherein $R^3$ is a cycloalkyl having 6-12 ring carbons.

Embodiment 68

The compound of Formula I, wherein $R^4$ is an alkyl group having 1-10 carbons.

Embodiment 69

The compound of Formula I, wherein $R^4$ is a cycloalkyl having 6-12 ring carbons.

Embodiment 70

The compound of Formula I or Formula II, wherein $R^5$ is an alkyl group having 1-10 carbons.

Embodiment 71

The compound of Formula I or Formula II, wherein $R^5$ is a cycloalkyl having 6-12 ring carbons.

Embodiment 72

The compound of Formula II, wherein $R^6$ is an alkyl group having 1-10 carbons.

Embodiment 73

The compound of Formula II, wherein $R^6$ is a cycloalkyl having 6-12 ring carbons.

Embodiment 74

The compound of any of Embodiments 66-73, wherein the alkyl group is deuterated.

Embodiment 75

The compound of Formula I or Formula II, wherein $R^3$ is a silyl group having the formula $R_3Si$—, where R is the same or different at each occurrence and is an alkyl group having 1-12 carbons.

Embodiment 76

The compound of Formula I, wherein $R^4$ is a silyl group having the formula $R_3Si$—, where R is the same or different at each occurrence and is an alkyl group having 1-12 carbons.

Embodiment 77

The compound of Formula I or Formula II, wherein $R^5$ is a silyl group having the formula $R_3Si$—, where R is the same or different at each occurrence and is an alkyl group having 1-12 carbons.

Embodiment 78

The compound of Formula II, wherein $R^6$ is a silyl group having the formula $R_3Si$—, where R is the same or different at each occurrence and is an alkyl group having 1-12 carbons.

Embodiment 79

The compound of any one of Embodiments 75-78, wherein the silyl group is deuterated.

Embodiment 80

The compound of Formula I or Formula II, wherein $R^3$ is aryl having 6-18 ring carbons.

Embodiment 81

The compound of Formula I, wherein $R^4$ is aryl having 6-18 ring carbons.

Embodiment 82

The compound of Formula I or Formula II, wherein $R^5$ is aryl having 6-18 ring carbons.

Embodiment 83

The compound of Formula II, wherein $R^6$ is aryl having 6-18 ring carbons.

Embodiment 84

The compound of any one of Embodiments 80-83, wherein the aryl group is deuterated.

Embodiment 85

The compound of Formula I or Formula II that exists as 100% fac and 0% mer structural isomers.

Embodiment 86

The compound of Formula I or Formula II that exists as 90% fac and 10% mer structural isomers.

Embodiment 87

The compound of Formula I or Formula II that exists as 80% fac and 20% mer structural isomers.

Embodiment 88

The compound of Formula I or Formula II that exists as 70% fac and 30% mer structural isomers.

Embodiment 89

The compound of Formula I or Formula II that exists as 60% fac and 40% mer structural isomers.

Embodiment 90

The compound of Formula I or Formula II that exists as 50% fac and 50% mer structural isomers.

Embodiment 91

The compound of Formula I or Formula II that exists as 40% fac and 60% mer structural isomers.

Embodiment 92

The compound of Formula I or Formula II that exists as 30% fac and 70% mer structural isomers.

Embodiment 93

The compound of Formula I or Formula II that exists as 20% fac and 80% mer structural isomers.

Embodiment 94

The compound of Formula I or Formula II that exists as 10% fac and 90% mer structural isomers.

Embodiment 95

The compound of Formula I or Formula II that exists as 0% fac and 100% mer structural isomers.

Any of the above general and specific embodiments can be combined with one or more of the other embodiments, so long as they are not mutually exclusive. For example, the embodiment in which Ar is phenyl can be combined with the embodiment in which $R^1$ is a cycloalkyl having 6-12 ring carbons. The same is true for the other non-mutually-exclusive embodiments discussed above. The skilled person would understand which embodiments were mutually exclusive and would thus readily be able to determine the combinations of embodiments that are contemplated by the present application.

Examples of materials having Formula I and Formula II include, but are not limited to, the compounds below, all of which may exist as either fac or mer structural isomers, including mixtures of both.

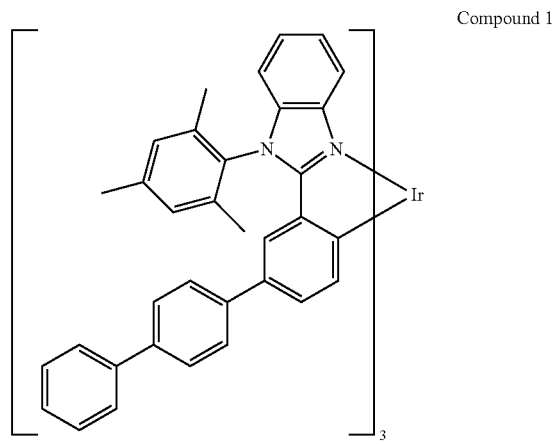

Compound 1

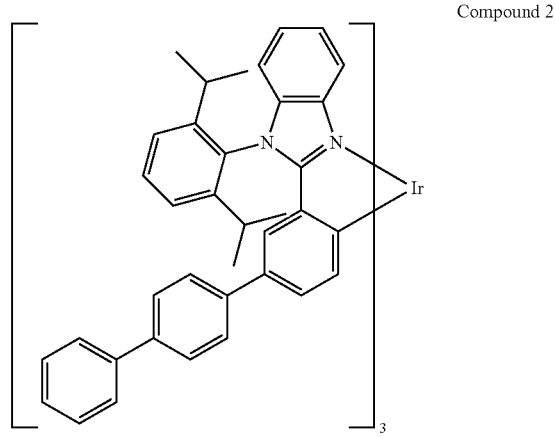

Compound 2

-continued
Compound 3
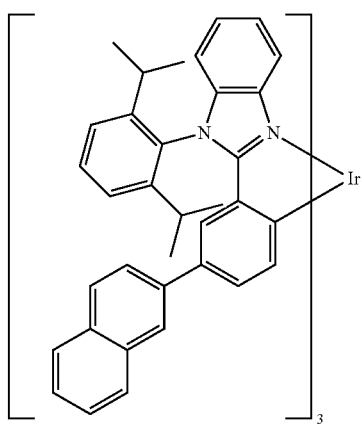
Compound 4
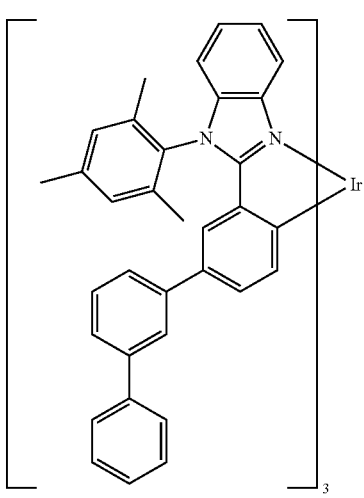
Compound 5
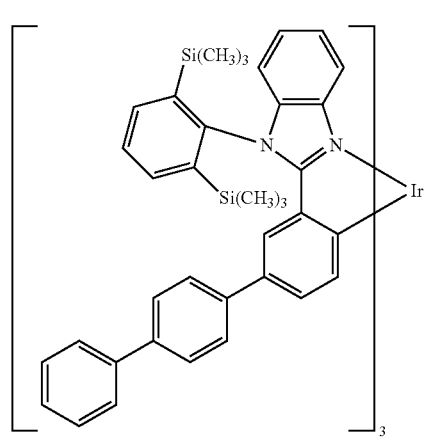
Compound 6
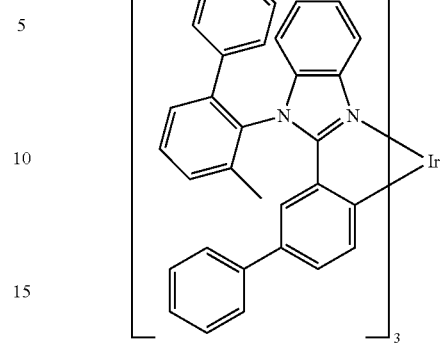
Compound 7
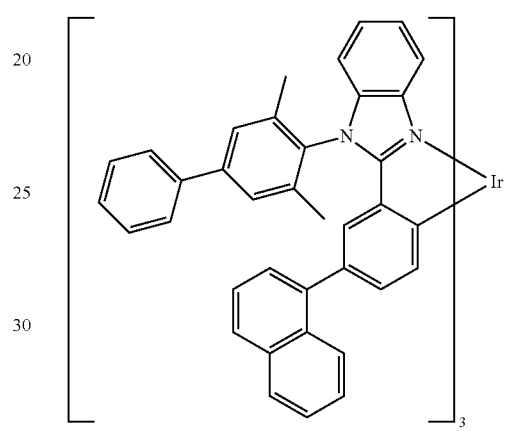
Compound 8
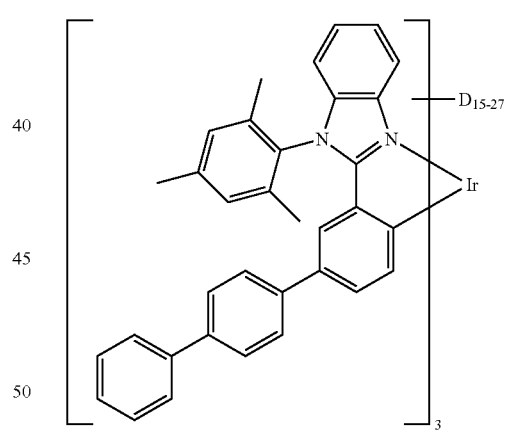
Compound 9
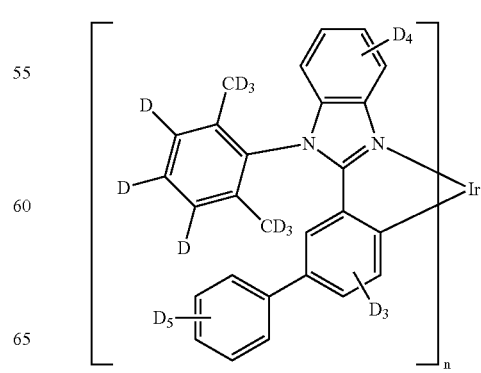

Compound 10
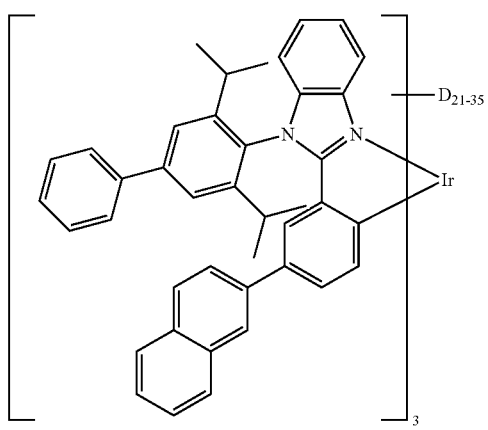
Compound 11
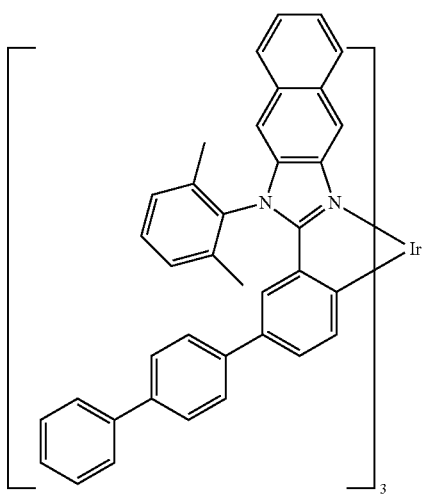
Compound 12
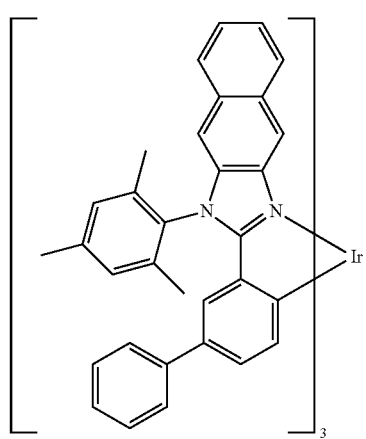
Compound 13
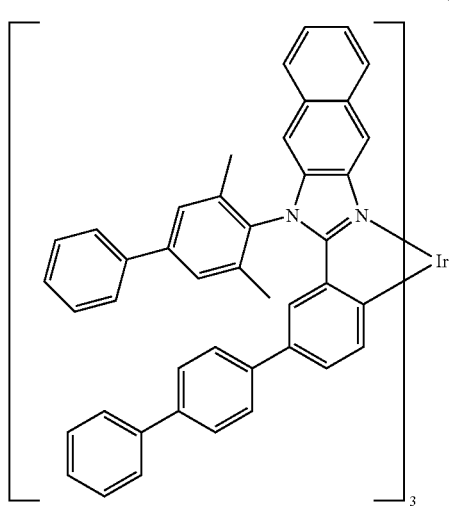
Compound 14
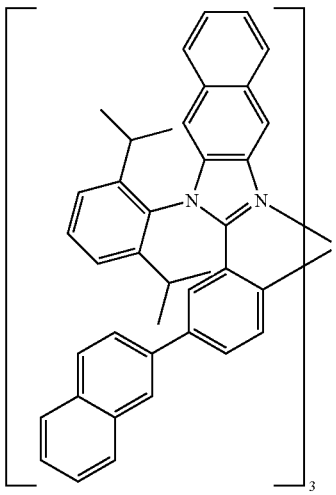
Compound 15
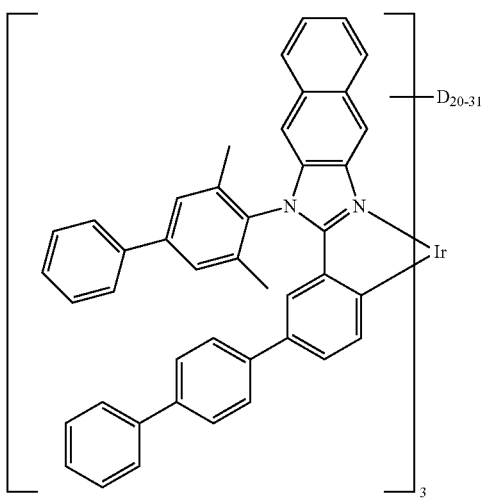

Compound 16

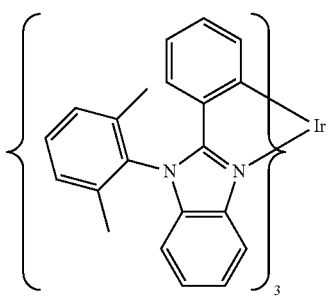

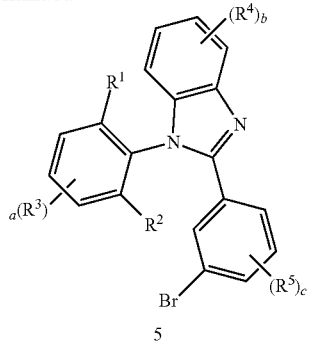

3. Synthesis

The materials described herein, are generally prepared by a procedure as follows. The ligand may be prepared via a route outlined as below:

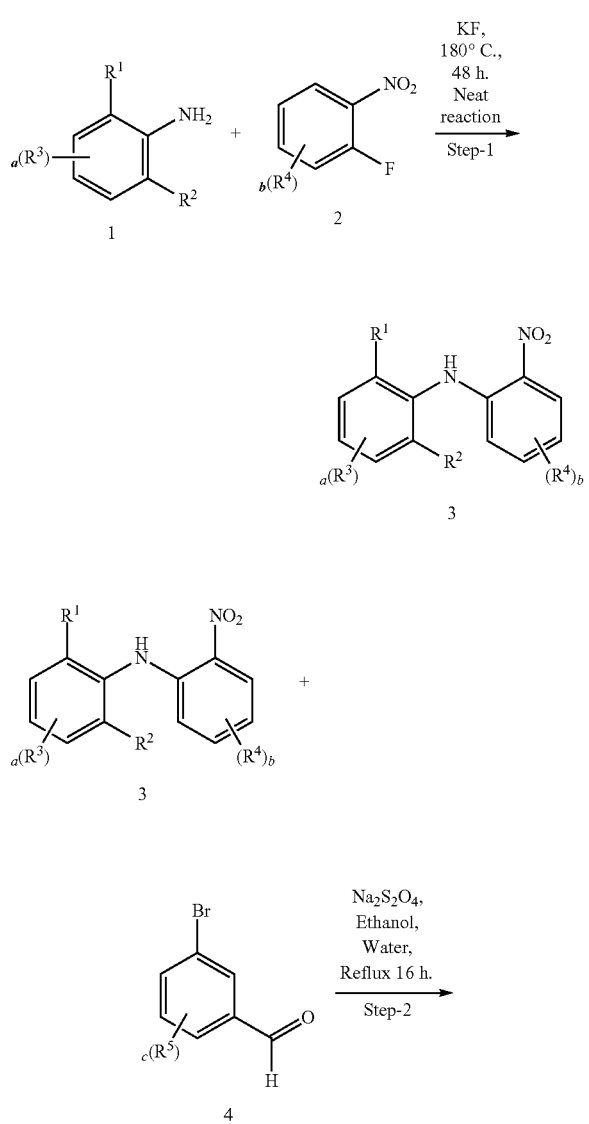

Aniline1 and 2-fluoronitrobenzene 2 are mixed together with potassium fluoride and heated in the absence of solvent at 180 C for 48 hrs. The resulting secondary amine 3 is isolated and reacted with the 3-bromobenzaldehyde 4 in the presence of sodium dithionite at reflux for 16 hrs. The bromo compound 5 is isolated and then reacted with an aryl boronic acid or ester using standard Pd catalysis to replace the bromo substituent with the desired aryl group. The resulting benzimidazole ligand is isolated by flash chromatography and dried and recovered for use to make the iridium complexes.

The ligand is then cyclometallated onto Ir using iridium trichloride in 2-ethoxyethanol at reflux to create the chlorodimeric intermediate. This step is followed by the third cyclometallization in alcohol solvent using silver salts to remove remaining chloride from the coordination sphere of the Ir. The isolated tris-cyclometallated material may be purified using chromatography, eluting with toluene or methylene chloride eluents and finally isolated by recrystallization from toluene or methylene chloride by addition of acetonitrile. The final yellow crystalline material is dried in high vacuum and then used, as isolated, in device construction. Individual details are presented below for specific compounds 1, 2 and 3.

If a mixture of fac and mer isomers is produced in the final cyclometallization step, separation into the two pure isomers may be carried out using simple column chromatography on silica gel. The general procedure is to first dissolve the isomeric mixture into a minimum volume of dry toluene with heat, if necessary. A chromatography column is then packed with a slurry of silica gel in toluene solvent and allowed to drain and settle. The toluene solution of isomers is loaded onto the top of the column and eluted with toluene under gravity feed. The mer isomer generally will run through this column faster and elute first and may be collected in the first fractions. Later fractions become enriched in the fac isomer. Monitoring PL with 365 nm light allows distinction of the separate bands from the mer and fac isomers. Evaporation of the pure fractions and addition of methanol will generate precipitates of the purified isomers which may be collected by fitration and dried prior to device testing.

4. Devices

Organic electronic devices that may benefit from having one or more layers including the materials described herein include, but are not limited to, (1) devices that convert electrical energy into radiation (e.g., a light-emitting diode, light emitting diode display, lighting device, luminaire, or diode laser), (2) devices that detect signals through electronics processes (e.g., photodetectors, photoconductive cells, photoresistors, photoswitches, phototransistors, phototubes, IR detectors, biosensors), (3) devices that convert radiation into electrical energy, (e.g., a photovoltaic device or solar cell), and (4) devices that include one or more electronic components that include one or more organic semi-conductor layers (e.g., a transistor or diode).

An exemplary illustration of an organic electronic device structure is shown in FIG. 1. The device 100 has a first electrical contact layer, an anode layer 110 and a second electrical contact layer, a cathode layer 160, and a photoactive layer 140 between them. Adjacent to the anode is a hole injection layer 120. Adjacent to the hole injection layer is a hole transport layer 130, including hole transport material. In some embodiments, there is an electron transport layer 150, including an electron transport material. As an option, devices may have an anti-quenching layer (not shown) between the photoactive layer 140 and the electron transport layer 150. As a further option, devices may use one or more additional hole injection or hole transport layers (not shown) next to the anode 110 and/or one or more additional electron injection or electron transport layers (not shown) next to the cathode 160.

Layers 120 through 150 are individually and collectively referred to as the active layers.

Figure 2:
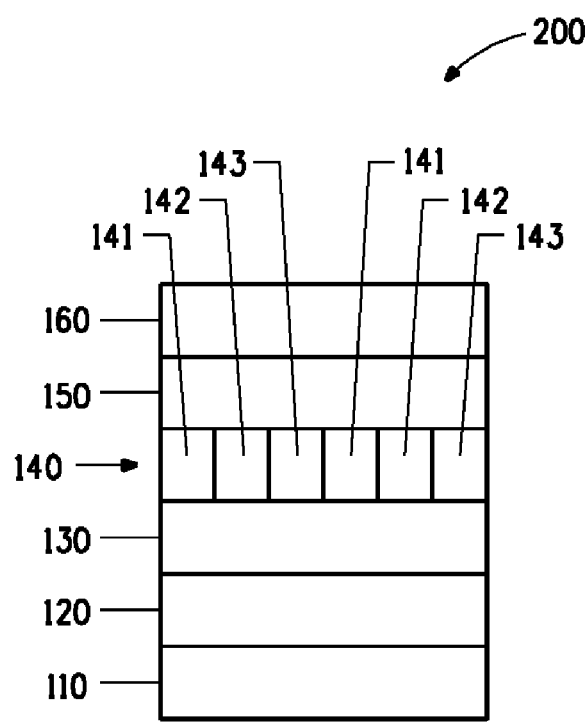
FIG. 2 includes another illustration of an organic light-emitting device.

In some embodiments, the photoactive layer is pixellated, as shown in FIG. 2. In device 200, layer 140 is divided into pixel or subpixel units 141, 142, and 143 which are repeated over the layer. Each of the pixel or subpixel units represents a different color. In some embodiments, the subpixel units are for red, green, and blue. Although three subpixel units are shown in the figure, two or more than three may be used.

In some embodiments, the different layers have the following range of thicknesses: anode 110, 500-5000 Å, in some embodiments, 1000-2000 Å; hole injection layer 120, 50-3000 Å, in some embodiments, 200-1000 Å; hole transport layer 120, 50-2000 Å, in some embodiments, 200-1000 Å; photoactive layer 130, 10-2000 Å, in some embodiments, 100-1000 Å; layer 140, 50-2000 Å, in some embodiments, 100-1000 Å; cathode 150, 200-10000 Å, in some embodiments, 300-5000 Å. The location of the electron-hole recombination zone in the device, and thus the emission spectrum of the device, can be affected by the relative thickness of each layer. The desired ratio of layer thicknesses will depend on the exact nature of the materials used.

In some embodiments, the compounds having Formula I are useful as the emissive material in photoactive layer 140, having green emission color. They can be used alone or as a dopant in a host material.

In some embodiments, the compounds having Formula I are useful as the emissive material in photoactive layer 140, having red emission color. They can be used alone or as a dopant in a host material.

In some embodiments, the compounds having Formula I are useful as a hole-trap in photoactive layer 140.

In some embodiments, the compound having Formula I are useful as an electron-trap in photoactive layer 140.

Any of the compounds of Formula I or Formula II represented by the embodiments and combination of embodiments discussed above can be used in the device.

a. Photoactive Layer

In some embodiments, the photoactive layer includes primarily a compound having Formula I, where components that would materially alter the function, the principle of operation, or the distinguishing characteristics of the layer are not present.

In some embodiments, the photoactive layer includes a host material and a compound having Formula I as a dopant.

In some embodiments, the photoactive layer includes a first host material, a compound having Formula I as a dopant, and a second host material.

In some embodiments, the photoactive layer includes primarily a host material and a compound having Formula I as a dopant, where components that would materially alter the function, the principle of operation, or the distinguishing characteristics of the layer are not present.

In some embodiments, the photoactive layer includes primarily a first host material, a second host material, and a compound having Formula I as a dopant, where components that would materially alter the function, the principle of operation, or the distinguishing characteristics of the layer are not present.

In some embodiments, the weight ratio of dopant having Formula I to total host material is in the range of 1:99 to 40:60; in some embodiments 5:95 to 30:70; in some embodiments, 10:90 to 20:80.

In some embodiments, the host has a triplet energy level higher than that of the dopant, so that it does not quench the emission. In some embodiments, the host is selected from the group including only carbazoles, indolocarbazoles, triazines, aryl ketones, phenylpyridines, pyrimidines, phenanthrenes, triarylamines, triphenylenes, thiophenes, furans, deuterated analogs thereof, combinations thereof, and mixtures thereof.

In some embodiments, the photoactive layer includes a luminescent compound, a host material, and a compound having Formula I as a hole-trap material.

In some embodiments, the photoactive layer includes a phosphorescent compound, a host material, and a compound having Formula I as a hole-trap material.

In some embodiments, the photoactive layer includes a phosphorescent cyclometallated complex, a host material, and a compound having Formula I as a hole-trap material.

In some embodiments, the photoactive layer includes a luminescent compound, a host material, and a compound having Formula I as a hole-trap material, and the luminescent compound has red, orange or yellow emission color.

In some embodiments, the photoactive layer includes a luminescent compound, a host material, a compound having Formula I as a hole-trap material, and a second host material.

In some embodiments, the photoactive layer includes primarily a luminescent compound, a host material, and a compound having Formula I as a hole-trap material, where components that would materially alter the function, the principle of operation, or the distinguishing characteristics of the layer are not present.

In some embodiments, the photoactive layer includes primarily a red luminescent compound, a host material, and a compound having Formula I as a hole-trap material, where components that would materially alter the function, the principle of operation, or the distinguishing characteristics of the layer are not present.

In some embodiments, the photoactive layer includes primarily a luminescent compound, a first host material, a second host material, and a compound having Formula I as a hole-trap material, where components that would materially alter the function, the principle of operation, or the distinguishing characteristics of the layer are not present.

In some embodiments, the photoactive layer includes primarily a red luminescent compound, a first host material, a second host material, and a compound having Formula I as a hole-trap material, where components that would materially alter the function, the principle of operation, or the distinguishing characteristics of the layer are not present.

The hole-trap material of Formula I can be present in an amount of 1-10 wt % based on the total weight of the layer; in some embodiments, 2-5 wt %.

The compounds having Formula I can be used as a hole-trap for any kind of electroluminescent ("EL") layer for which any of the component HOMO levels are further from the vacuum level as compared to the HOMO level of the compound of Formula I. In addition, for fluorescent emissive materials, the first emissive singlet energy state should be lower in energy than the first excited singlet energy state of the compound of Formula I.

EL materials include, but are not limited to, small molecule organic fluorescent compounds, luminescent metal complexes, conjugated polymers, and mixtures thereof. Examples of fluorescent compounds include, but are not limited to, chrysenes, pyrenes, perylenes, rubrenes, coumarins, anthracenes, thiadiazoles, derivatives thereof, arylamino derivatives thereof, and mixtures thereof. Examples of metal complexes include, but are not limited to, metal chelated oxinoid compounds, such as tris(8-hydroxyquinolato)aluminum (Alq3), cyclometalated iridium and platinum electroluminescent compounds, such as complexes of iridium with phenylpyridine, phenylquinoline, or phenylpyrimidine ligands as disclosed in Petrov et al., U.S. Pat. No. 6,670,645 and Published PCT Applications WO 03/063555 and WO 2004/016710, and organometallic complexes described in, for example, Published PCT Applications WO 03/008424, WO 03/091688, and WO 03/040257, and mixtures thereof. Examples of conjugated polymers include, but are not limited to poly(phenylenevinylenes), polyfluorenes, poly(spirobifluorenes), polythiophenes, poly(p-phenylenes), copolymers thereof, and mixtures thereof.

Examples of red, orange and yellow light-emitting materials include, but are not limited to, complexes of Ir having phenylquinoline or phenylisoquinoline ligands, periflanthenes, fluoranthenes, and perylenes. Red light-emitting materials have been disclosed in, for example, U.S. Pat. No. 6,875,524, and published US application 2005-0158577.

In some embodiments, the photoactive layer includes a luminescent compound, a host material, and a compound having Formula I as an electron-trap material.

In some embodiments, the photoactive layer includes a phosphorescent compound, a host material, and a compound having Formula I as an electron-trap material.

In some embodiments, the photoactive layer includes a phosphorescent cyclometallated complex, a host material, and a compound having Formula I as an electron-trap material.

In some embodiments, the photoactive layer includes a luminescent compound, a host material, and a compound having Formula I as an electron-trap material, and the luminescent compound has red, orange or yellow emission color.

In some embodiments, the photoactive layer includes a luminescent compound, a host material, a compound having Formula I as an electron-trap material, and a second host material.

In some embodiments, the photoactive layer includes primarily a luminescent compound, a host material, and a compound having Formula I as an electron-trap material, where components that would materially alter the function, the principle of operation or the distinguishing characteristics of the layer are not present.

In some embodiments, the photoactive layer includes primarily a red luminescent compound, a host material, and a compound having Formula I as an electron-trap material, where components that would materially alter the function, the principle of operation or the distinguishing characteristics of the layer are not present.

In some embodiments, the photoactive layer includes primarily a luminescent compound, a first host material, a second host material, and a compound having Formula I as an electron-trap material, where components that would materially alter the function, the principle of operation or the distinguishing characteristics of the layer are not present.

In some embodiments, the photoactive layer includes primarily a red luminescent compound, a first host material, a second host material, and a compound having Formula I as an electron-trap material, where components that would materially alter the function, the principle of operation or the distinguishing characteristics of the layer are not present.

The electron-trap material of Formula I can be present in an amount of 1-10 wt % based on the total weight of the layer; in some embodiments, 2-5 wt %.

The compounds having Formula I can be used as an electron-trap for any kind of electroluminescent ("EL") layer for which any of the component LUMO levels are closer to the vacuum level as compared to the LUMO level of the compound of Formula I. In addition, for fluorescent emissive materials, the first emissive singlet energy state should be lower in energy than the first excited singlet energy state of the compound of Formula I.

b. Other Device Layers

The other layers in the device can be made of any materials which are known to be useful in such layers.

The anode 110 is an electrode that is particularly efficient for injecting positive charge carriers. It can be made of, for example, materials containing a metal, mixed metal, alloy, metal oxide or mixed-metal oxide, or it can be a conducting polymer, and mixtures thereof. Suitable metals include the Group 11 metals, the metals in Groups 4, 5, and 6, and the Group 8-10 transition metals. If the anode is to be light-transmitting, mixed-metal oxides of Groups 12, 13 and 14 metals, such as indium-tin-oxide, are generally used. The anode may also include an organic material such as polyaniline as described in "Flexible light-emitting diodes made from soluble conducting polymer," Nature vol. 357, pp 477-479 (11 Jun. 1992). At least one of the anode and cathode should be at least partially transparent to allow the generated light to be observed.

The hole injection layer 120 includes hole injection material and may have one or more functions in an organic electronic device, including but not limited to, planarization of the underlying layer, charge transport and/or charge injection properties, scavenging of impurities such as oxygen or metal ions, and other aspects to facilitate or to improve the performance of the organic electronic device. The hole injection layer can be formed with polymeric materials, such as polyaniline (PANI) or polyethylenedioxythiophene (PEDOT), which are often doped with protonic acids. The protonic acids can be, for example, poly(styrenesulfonic acid), poly(2-acrylamido-2-methyl-1-propanesulfonic acid), and the like.

The hole injection layer can include charge transfer compounds, and the like, such as copper phthalocyanine and the tetrathiafulvalene-tetracyanoquinodimethane system (TTF-TCNQ).

In some embodiments, the hole injection layer includes at least one electrically conductive polymer and at least one fluorinated acid polymer.

In some embodiments, the hole injection layer is made from an aqueous dispersion of an electrically conducting polymer doped with a colloid-forming polymeric acid. Such materials have been described in, for example, published U.S. patent applications US 2004/0102577, US 2004/0127637, US 2005/0205860, and published PCT application WO 2009/018009.

Examples of hole transport materials for layer 130 have been summarized for example, in Kirk-Othmer Encyclopedia of Chemical Technology, Fourth Edition, Vol. 18, p. 837-860, 1996, by Y. Wang. Both hole transporting molecules and polymers can be used. Commonly used hole transporting molecules are: N,N'-diphenyl-N,N'-bis(3-methylphenyl)-[1,1'-biphenyl]-4,4'-diamine (TPD), 1,1-bis[(di-4-tolylamino) phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis-(3-methylphenyl)-N,N,N',N'-2,5-phenylenediamine (PDA), a-phenyl-4-N,N-diphenylaminostyrene (TPS), p-(diethylamino) benzaldehyde diphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl] pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), N,N'-bis(naphthalen-1-yl)-N,N'-bis-(phenyl)benzidine (α-NPB), and porphyrinic compounds, such as copper phthalocyanine. In some embodiments, the hole transport layer includes a hole transport polymer. In some embodiments, the hole transport polymer is a distyrylaryl compound. In some embodiments, the aryl group has two or more fused aromatic rings. In some embodiments, the aryl group is an acene. The term "acene" as used herein refers to a hydrocarbon parent component that contains two or more ortho-fused benzene rings in a straight linear arrangement. Other commonly used hole transporting polymers are polyvinylcarbazole, (phenylmethyl)-polysilane, and polyaniline. It is also possible to obtain hole transporting polymers by doping hole transporting molecules such as those mentioned above into polymers such as polystyrene and polycarbonate. In some cases, triarylamine polymers are used, especially triarylamine-fluorene copolymers. In some cases, the polymers and copolymers are crosslinkable.

In some embodiments, the hole transport layer further includes a p-dopant. In some embodiments, the hole transport layer is doped with a p-dopant. Examples of p-dopants include, but are not limited to, tetrafluorotetracyanoquinodimethane (F4-TCNQ) and perylene-3,4,9,10-tetracarboxylic-3,4,9,10-dianhydride (PTCDA).

Examples of electron transport materials which can be used for layer 150 include, but are not limited to, metal chelated oxinoid compounds, including metal quinolate derivatives such as tris(8-hydroxyquinolato)aluminum (AlQ), bis(2-methyl-8-quinolinolato)(p-phenylphenolato)aluminum (BAlq), tetrakis-(8-hydroxyquinolato)hafnium (HfQ) and tetrakis-(8-hydroxyquinolato)zirconium (ZrQ); and azole compounds such as 2-(4-biphenylyl)-5-(4-t-butylphenyl)-1,3,4-oxadiazole (PBD), 3-(4-biphenylyl)-4-phenyl-5-(4-t-butylphenyl)-1,2,4-triazole (TAZ), and 1,3,5-tri(phenyl-2-benzimidazole)benzene (TPBI); quinoxaline derivatives such as 2,3-bis(4-fluorophenyl)quinoxaline; phenanthrolines such as 4,7-diphenyl-1,10-phenanthroline (DPA) and 2,9-dimethyl-4,7-diphenyl-1,10-phenanthroline (DDPA); and mixtures thereof. In some embodiments, the electron transport layer further includes an n-dopant. N-dopant materials are well known. The n-dopants include, but are not limited to, Group 1 and 2 metals; Group 1 and 2 metal salts, such as LiF, CsF, and $Cs_2CO_3$; Group 1 and 2 metal organic compounds, such as Li quinolate; and molecular n-dopants, such as leuco dyes, metal complexes, such as $W_2(hpp)_4$ where hpp=1,3,4,6,7,8-hexahydro-2H-pyrimido-[1,2-a]-pyrimidine and cobaltocene, tetrathianaphthacene, bis(ethylenedithio)tetrathiafulvalene, heterocyclic radicals or diradicals, and the dimers, oligomers, polymers, dispiro compounds and polycycles of heterocyclic radical or diradicals.

In some embodiments, an anti-quenching layer may be present between the photoactive layer and the electron transport layer to prevent quenching of luminance by the electron transport layer. To prevent energy transfer quenching, the singlet energy of the anti-quenching material has to be higher than the singlet energy of the emitter. To prevent electron transfer quenching, the LUMO level of the anti-quenching material has to be shallow enough (with respect to the vacuum level) such that electron transfer between the emitter exciton and the anti-quenching material is endothermic. Furthermore, the HOMO level of the anti-quenching material has to be deep enough (with respect to the vacuum level) such that electron transfer between the emitter exciton and the anti-quenching material is endothermic. In general, anti-quenching material is a large band-gap material with high singlet and triplet energies.

The cathode 160, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used.

Alkali metal-containing inorganic compounds, such as LiF, CsF, $Cs_2O$ and $Li_2O$, or Li-containing organometallic or coordination compounds can also be deposited between the organic layer 150 and the cathode layer 160 to lower the operating voltage. This layer, not shown, may be referred to as an electron injection layer.

It is known to have other layers in organic electronic devices. For example, there can be a layer (not shown) between the anode 110 and hole injection layer 120 to control the amount of positive charge injected and/or to provide band-gap matching of the layers, or to function as a protective layer. Layers that are known in the art can be used, such as copper phthalocyanine, silicon oxy-nitride, fluorocarbons, silanes, or an ultra-thin layer of a metal, such as Pt. Alternatively, some or all of anode layer 110, active layers 120, 130, 140, and 150, or cathode layer 160, can be surface-treated to increase charge carrier transport efficiency. The choice of materials for each of the component layers is preferably determined by balancing the positive and negative charges in the emitter layer to provide a device with high electroluminescence efficiency.

It is understood that each functional layer can be made up of more than one layer.

c. Device Fabrication

The device layers can be formed by any deposition technique, or combinations of techniques, including vapor deposition, liquid deposition, and thermal transfer.

In some embodiments, the device is fabricated by liquid deposition of the hole injection layer, the hole transport layer, and the photoactive layer, and by vapor deposition of the anode, the electron transport layer, an electron injection layer and the cathode.

The hole injection layer can be deposited from any liquid medium in which it is dissolved or dispersed and from which it will form a film. In some embodiments, the liquid medium includes primarily one or more organic solvents, where components that would materially alter the function, the principle of operation or the distinguishing characteristics of the medium are not present.

In some embodiments, the liquid medium includes primarily water or water and an organic solvent, where components that would materially alter the function, the principle of operation or the distinguishing characteristics of the medium are not present.

The hole injection material can be present in the liquid medium in an amount from 0.5 to 10 percent by weight. The hole injection layer can be applied by any continuous or discontinuous liquid deposition technique. In some embodiments, the hole injection layer is applied by spin coating. In some embodiments, the hole injection layer is applied by ink jet printing. In some embodiments, the hole injection layer is applied by continuous nozzle printing. In some embodiments, the hole injection layer is applied by slot-die coating. After liquid deposition, the liquid medium can be removed in air, in an inert atmosphere, or by vacuum, at room temperature or with heating.

The hole transport layer can be deposited from any liquid medium in which it is dissolved or dispersed and from which it will form a film. In some embodiments, the liquid medium includes primarily one or more organic solvents, where components that would materially alter the function, the principle of operation or the distinguishing characteristics of the medium are not present.

In some embodiments, the liquid medium includes primarily water or water and an organic solvent, where components that would materially alter the function, the principle of operation or the distinguishing characteristics of the medium are not present.

In some embodiments, the organic solvent is an aromatic solvent. In some embodiments, the organic liquid is selected from chloroform, dichloromethane, chlorobenzene, dichlorobenzene, toluene, xylene, mesitylene, anisole, and mixtures thereof. The hole transport material can be present in the liquid medium in a concentration of 0.2 to 2 percent by weight. The hole transport layer can be applied by any continuous or discontinuous liquid deposition technique. In some embodiments, the hole transport layer is applied by spin coating. In some embodiments, the hole transport layer is applied by ink jet printing. In some embodiments, the hole transport layer is applied by continuous nozzle printing. In some embodiments, the hole transport layer is applied by slot-die coating. After liquid deposition, the liquid medium can be removed in air, in an inert atmosphere, or by vacuum, at room temperature or with heating.

The photoactive layer can be deposited from any liquid medium in which it is dissolved or dispersed and from which it will form a film. In some embodiments, the liquid medium includes primarily one or more organic solvents, where components that would materially alter the function, the principle of operation or the distinguishing characteristics of the medium are not present.

In some embodiments, the liquid medium includes primarily water or water and an organic solvent, where components that would materially alter the function, the principle of operation or the distinguishing characteristics of the medium are not present.

In some embodiments, the organic solvent is an aromatic solvent. In some embodiments, the organic solvent is selected from chloroform, dichloromethane, toluene, anisole, 2-butanone, 3-pentanone, butyl acetate, acetone, xylene, mesitylene, chlorobenzene, tetrahydrofuran, diethyl ether, trifluorotoluene, and mixtures thereof. The photoactive material can be present in the liquid medium in a concentration of 0.2 to 2 percent by weight. Other weight percentages of photoactive material may be used depending upon the liquid medium. The photoactive layer can be applied by any continuous or discontinuous liquid deposition technique. In some embodiments, the photoactive layer is applied by spin coating. In some embodiments, the photoactive layer is applied by ink jet printing. In some embodiments, the photoactive layer is applied by continuous nozzle printing. In some embodiments, the photoactive layer is applied by slot-die coating. After liquid deposition, the liquid medium can be removed in air, in an inert atmosphere, or by vacuum, at room temperature or with heating.

The electron transport layer can be deposited by any vapor deposition method. In some embodiments, it is deposited by thermal evaporation under vacuum.

The electron injection layer can be deposited by any vapor deposition method. In some embodiments, it is deposited by thermal evaporation under vacuum.

The cathode can be deposited by any vapor deposition method. In some embodiments, it is deposited by thermal evaporation under vacuum.

EXAMPLES

The concepts described herein will be further described in the following examples, which do not limit the scope of the invention described in the claims.

Synthesis Example 1

This example illustrates the preparation of Compound 1.

Example 1

A Preparation of 1-[2,4,6-trimethyl)phenyl]-2-(3-bromophenyl)-1H-benzimidazole (Intermediate 5)

100 g of 2,4,6-trimethylaniline (reagent 1) was mixed with 55 g 2-fluoronitrobenzene (reagent 2) and 30 g potassium fluoride and heated to 180° C. under nitrogen for 24 hrs in the absence of any solvent. The resulting material was cooled and purified by column chromatography using 60-120 silica eluted gradually with 10% EtOAc+Hexane. 55 g (62%) intermediate material (3) was isolated with 99.7% purity as judged by HPLC.

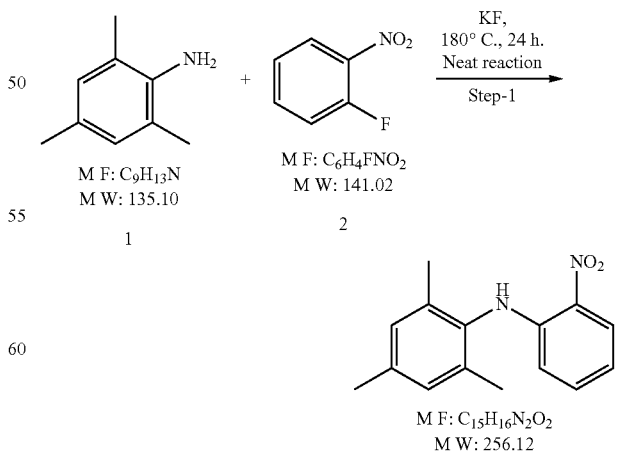

55 g intermediate (3) was mixed with 51.4 g 2-bromobenzaldehyde (reagent 4) and 3 eq $Na_2S_2O_4$ in 1.1 L 50/50 ethanol/water and refluxed under nitrogen for 16 hrs. The intermediate (5) product was isolated by column chromatography using 60-120 silica eluted gradually with 10% EtOAc+Hexane to yield 33.5 g (42%) having ~99% purity by HPLC.

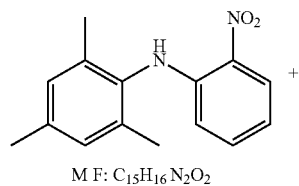

M F: $C_{15}H_{16}N_2O_2$
M W: 256.12

3

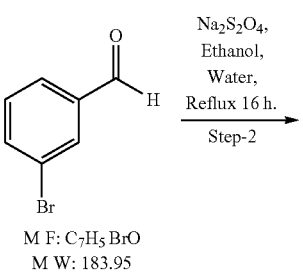

M F: $C_7H_5BrO$
M W: 183.95

4

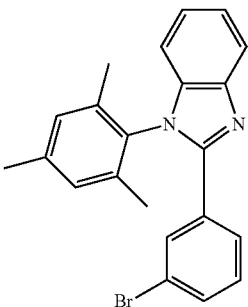

$C_{22}H_{19}BrN_2$
Mol. Wt.: 391.30

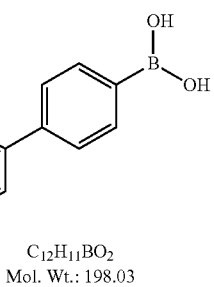

$C_{12}H_{11}BO_2$
Mol. Wt.: 198.03

M F: $C_{22}H_{19}BrN_2$
M W: 390.07)

5

Example 1B

Preparation of 1-[2,4,6-trimethyl)phenyl]-2-(3-(4-biphenyl))-1H-benzimidazole (Ligand 6)

1-[2,4,6-trimethyl)phenyl]-2-(3-bromophenyl)-1H-benzimidazole (intermediate 5 from example 1A above) (10.17 grams, 0.0260 mol), 4-biphenylboronic acid (6.33 grams, 0.0320 mol), water (40.7 ml.) and potassium carbonate (11.07 grams, 0.080 mol), and 203 ml. of monoglyme were sparged with nitrogen. Next, tris(dibenzylideneacetone) dipalladium(0), (1.186 grams, 1.296 mmol) and tricyclohexylphosphine (0.7266 grams, 2.591 mmol) were added quickly and the mixture refluxed overnight. The monoglyme was removed by rotary evaporation and dichloromethane/water partition was performed. The dichloromethane solution was pre-absorbed onto silica and purified by silica column chromatography with dichloromethane and hexanes. Product was concentrated by rotary evaporation to 9.47 grams of ligand 6 for a 78% yield.

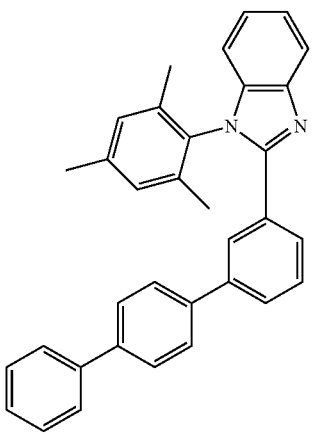

6

$C_{34}H_{28}N_2$
Mol. Wt.: 464.60

Example 1C

Preparation of Final Iridium Complex, (Compound 1)

Take 4.65 g ligand (6) from example 1B above, and add 1.8 g iridium chloride in 50 mL 2-ethoxyethanol, and 5 mL water. Reflux this mixture under nitrogen for 48 hrs then cool the thick dark yellow slurry. Evaporate, under vacuum, to dryness and dissolve the powdery orange yellow solid into methylene chloride and filter through celite. Take the deep yellow brown solution and add 1.8 g silver triflate and ~10% methanol and then stir well at 45° C. for 4 hrs. Cool, evaporate and extract into methylene chloride/methanol 8/2 and filter through celite to remove silver salts. Evaporate this solution to dryness and re-dissolve into 2-ethoxyethanol and add 3.9 g more ligand (6) then reflux this solution overnight.

Figure 3:
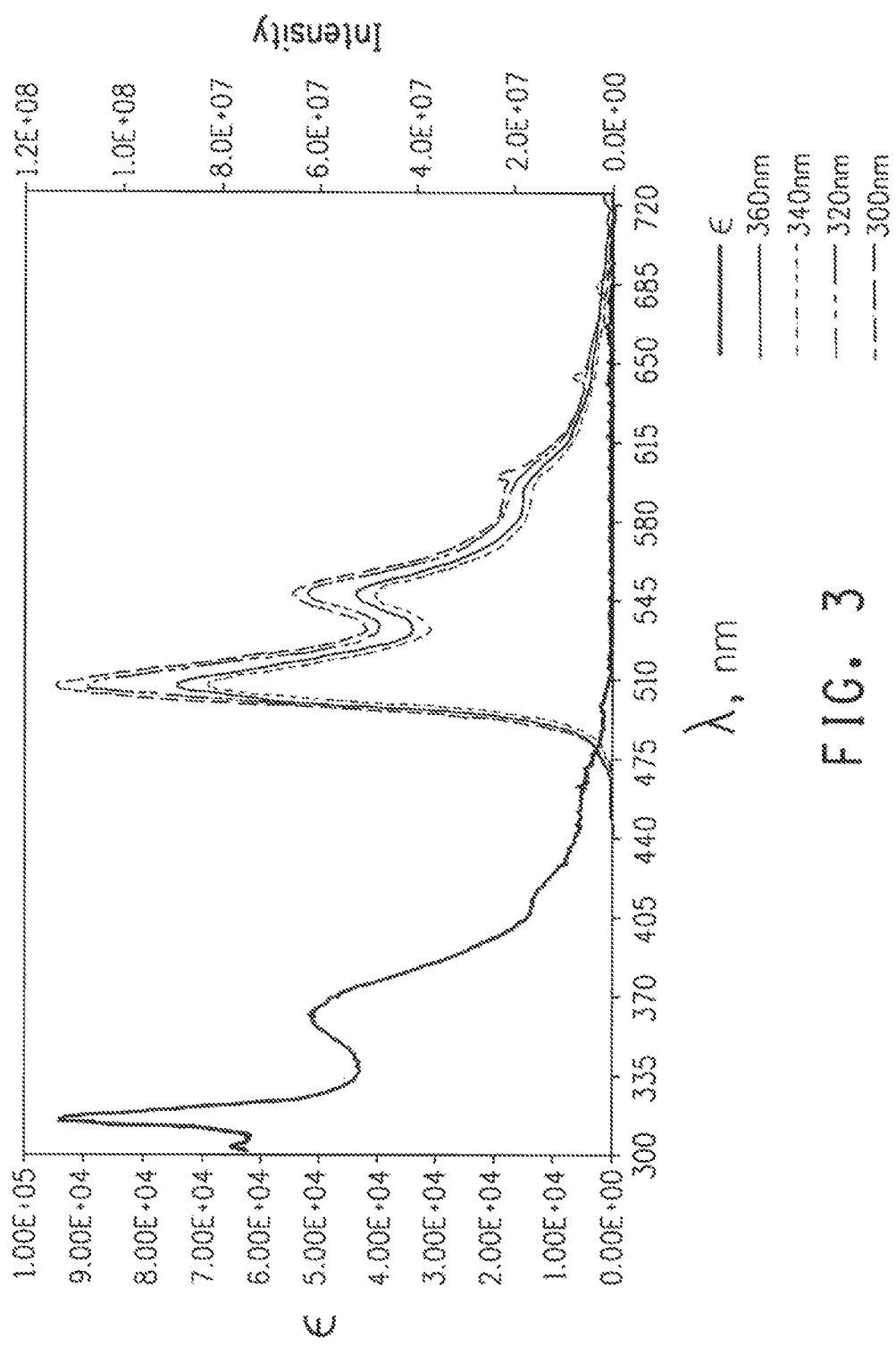
FIG. 3 includes emission spectra for Compound 1.

The solution generates a lot of solid at this point and is green luminescent. Evaporate this slurry in a nitrogen stream and dissolve the dark solid into toluene, filter and then run through a stacked column of β-alumina/α-aluminafilorisil to elute (toluene) a yellow orange solution. Collect the orange solution and evaporate to low volume (~50 mL) then add an equal volume of acetonitrile and leave to crystallize overnight. Filter and wash the bright yellow solid with methanol to collect a powdery yellow solid (3.3 g). Structure of the material was confirmed by 1-H nmr spectroscopy as being the tris cyclometallated fac isomer of the desired structure Compound 1. The photoluminescence spectrum is shown in FIG. 3, with a FWHM of 56 nm.

Synthesis Example 2

This example illustrates the preparation of Compound 2.

Example 2A

Preparation of 1-[2,6-di-i-propylphenyl]-2-(3-bromophenyl)-1H-benzimidazole (Intermediate 8)

The procedure given above for example 1A was followed with minor modification of materials as indicated here substituting reagent 7 for reagent 1:

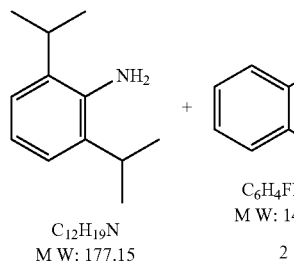

$C_{12}H_{19}N$
M W: 177.15

7

$C_6H_4FNO_2$
M W: 141.02

2

KF, 180° C., 48 h.
Neat reaction
Step-1

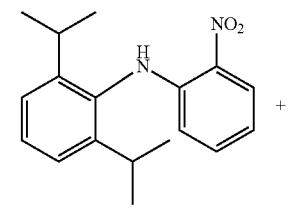

$C_{18}H_{22}N_2O_2$
M W: 298.17

3

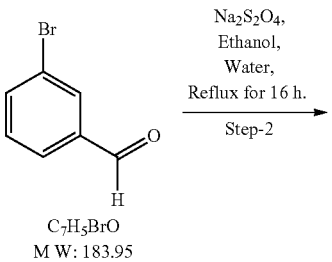

$C_7H_5BrO$
M W: 183.95

4

$Na_2S_2O_4$,
Ethanol,
Water,
Reflux for 16 h.
Step-2

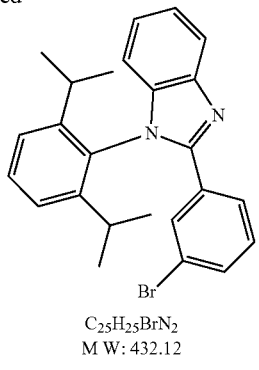

$C_{25}H_{25}BrN_2$
M W: 432.12

8

Example 2B

Preparation of 1-[2,6-di-i-propylphenyl]-2-(3-(4-biphenyl))-1H-benzimidazole. (Ligand 9)

1-[2,6-bis(1-methylethyl)phenyl]-2-(3-bromophenyl)-1H-benzimidazole (intermediate 8 from above example 2A) (9.90 grams, 0.0228 mol), 4-biphenylboronic acid (5.50 grams, 0.0278 mol), water (39.6 ml.) and potassium carbonate (9.9 grams, 0.072 mol), and 198 ml. of monoglyme were sparged with nitrogen. Tris(dibenzylideneacetone)-dipalladium(0), (1.155 grams, 1.26 mmol) and tricyclohexylphosphine (0.707 grams, 2.52 mmol) were added quickly and the mixture refluxed under nitrogen overnight. The monoglyme was removed by rotary evaporation and methylene chloride/water partition was performed. The methylene chloride solution was preabsorbed onto silica gel and purified by silica column chromatography with methylene chloride and hexanes. Product was concentrated by rotary evaporation to 9.1 grams of ligand (9), 78% yield.

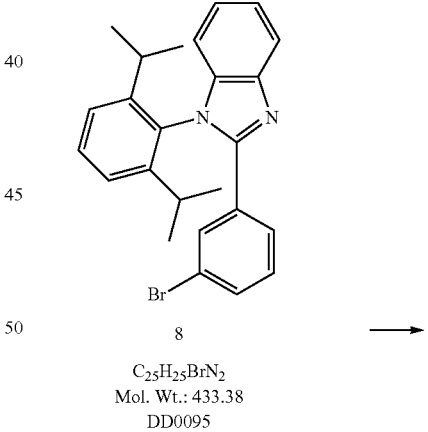

$C_{25}H_{25}BrN_2$
Mol. Wt.: 433.38
DD0095

8

→

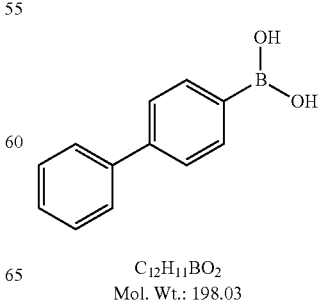

$C_{12}H_{11}BO_2$
Mol. Wt.: 198.03

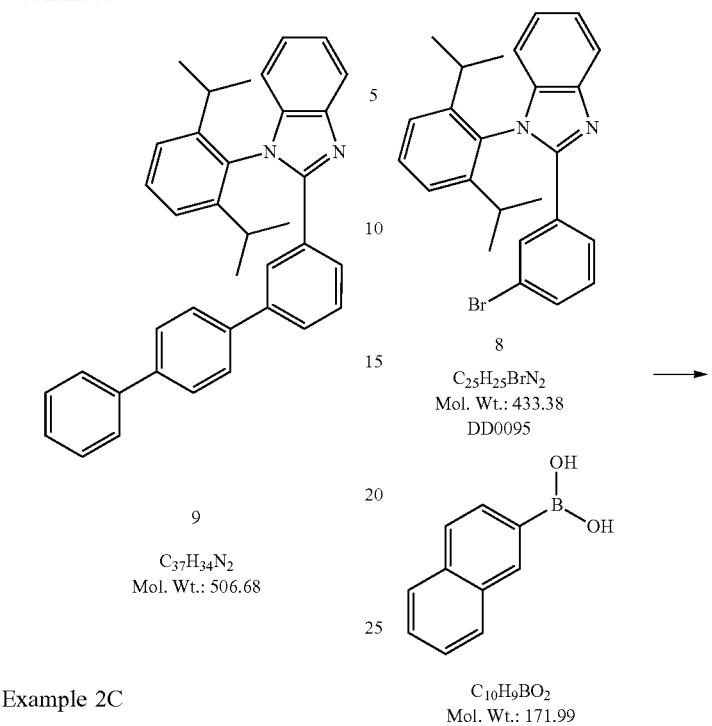

Example 2C

Preparation of Final Iridium Complex
(Compound 2)

Figure 4:
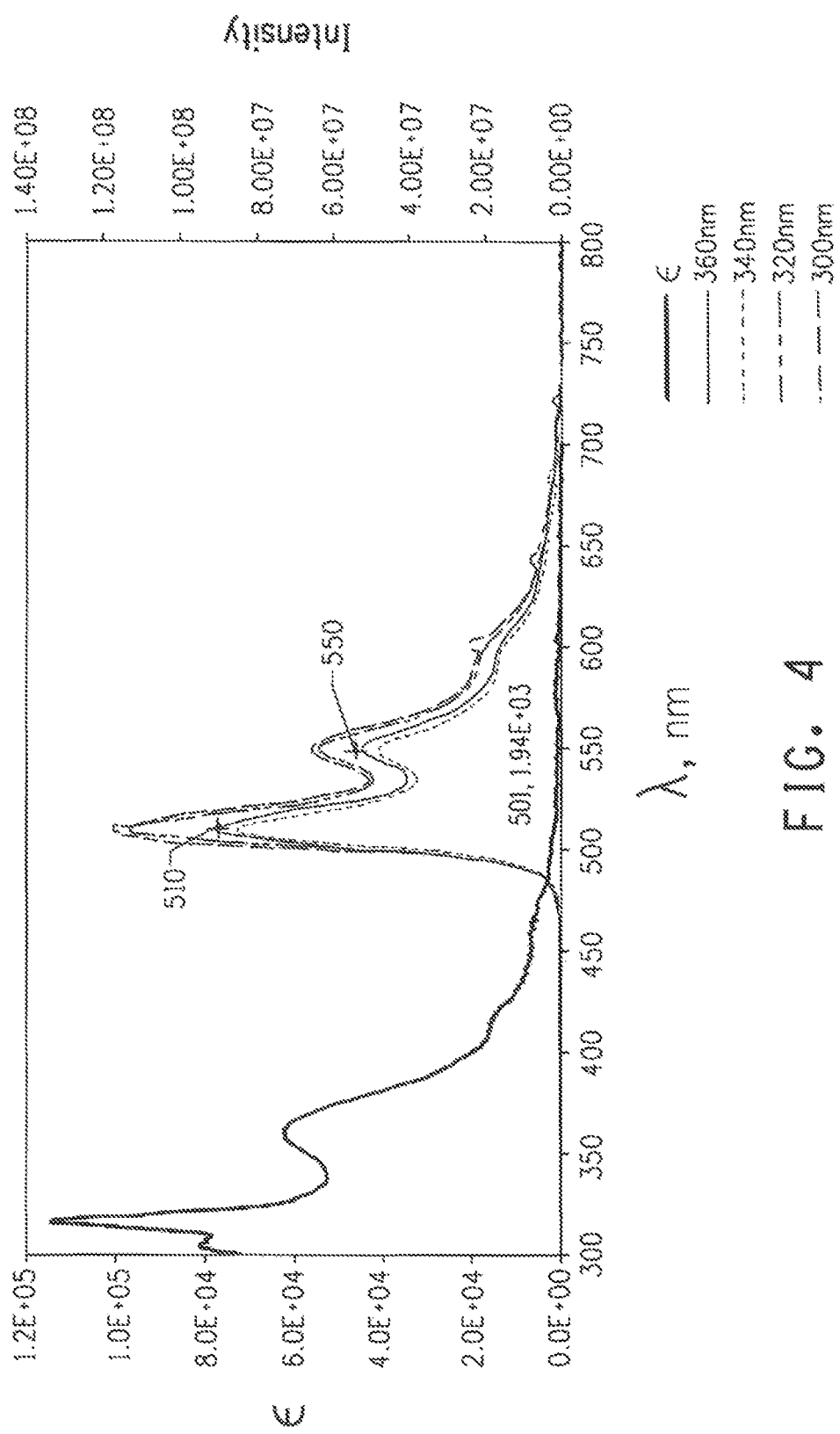
FIG. 4 includes emission spectra for Compound 2.

Ligand 9 from example 2B above was cyclometallated onto iridium in the same procedure as described in example 1C above. The Compound 2 material was identified as the tris cyclometallated fac isomer by 1-H nmr spectroscopy. The photoluminescence spectrum is shown in FIG. 4, with a FWHM of 56 nm.

Synthesis Example 3

This example illustrates the preparation of Compound 3.

Example 3A

Preparation of 1-[2,6-di-i-propylphenyl]-2-(3-(2-naphthyl))-1H-benzimidazole. (Ligand 10)

1-[2,6-bis(1-methylethyl)phenyl]-2-(3-bromophenyl)-1H-benzimidazole (intermediate 8 from example 2A above) (7.37 grams, 0.0172 mol), naphthalene-2-boronic acid (3.65 grams, 0.0212 mol), water (29.9 ml.) and potassium carbonate (7.47 grams, 0.054 mol), and 149 ml. of monoglyme were sparged with nitrogen. Next, Amphos ligand, (Aldrich 678740) (0.365 grams, 0.516 mmol) was added quickly and the mixture refluxed overnight. The monoglyme was removed by rotary evaporation and methylene chloride/water partition was performed. The methylene chloride solution was preabsorbed onto silica gel and purified by silica column chromatography with methylene chloride and hexanes. Product was concentrated by rotary evaporation to 8.1 grams of a dark glassy material, 97% yield. of ligand 10.

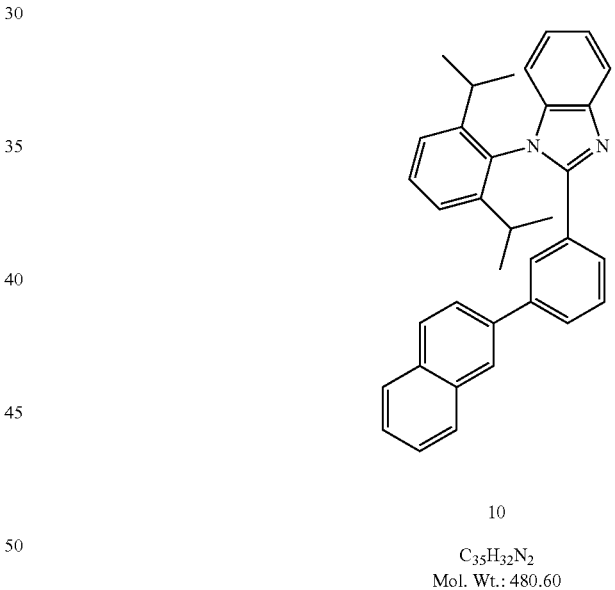

Example 3B

Preparation of Final Iridium Complex
(Compound 3)

Figure 5:
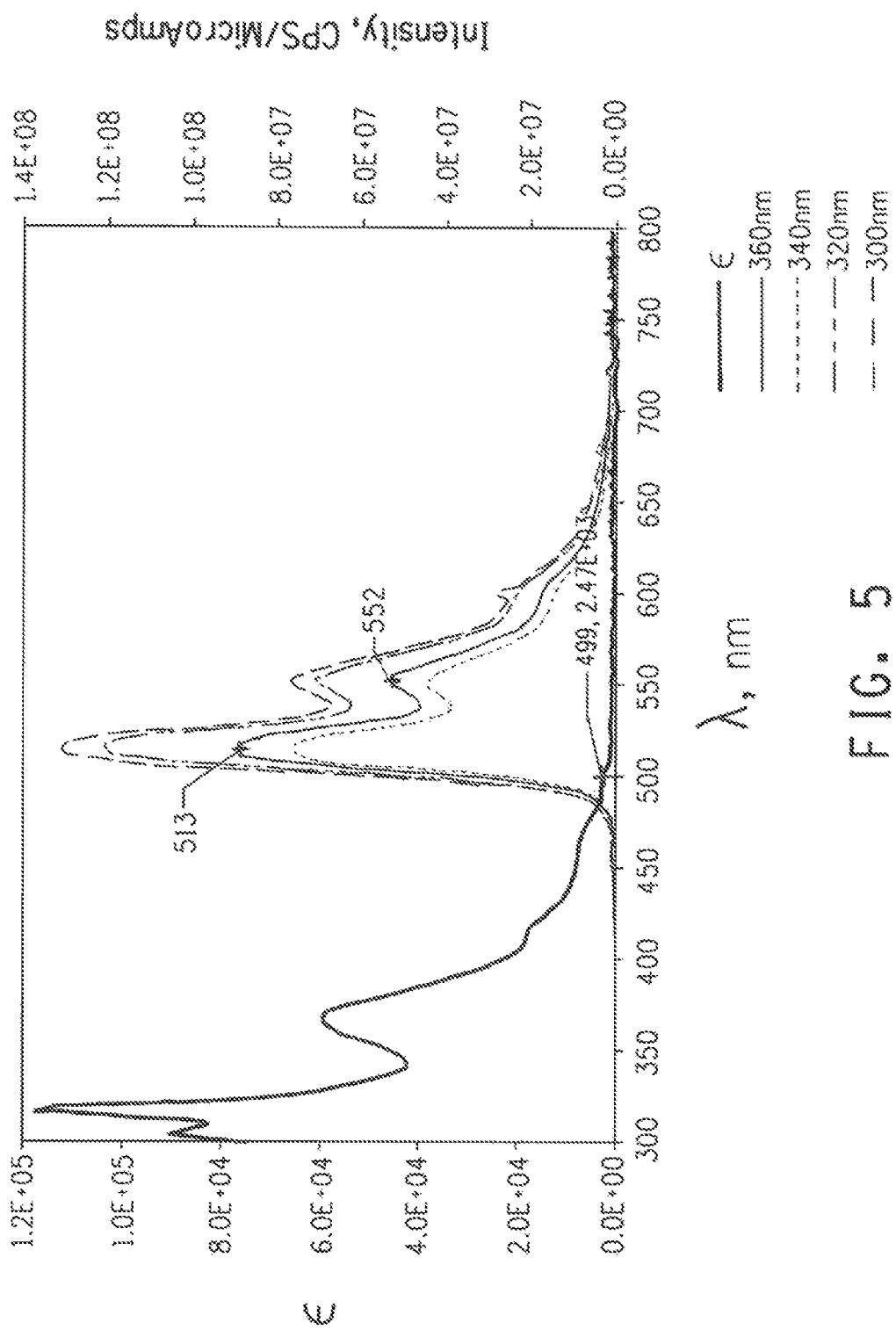
FIG. 5 includes emission spectra for Compound 3.

Ligand 10 from example 3A above was cyclometallated onto iridium in the same procedure as described in example 1C above. The Compound 3 material was identified as the tris cyclometallated fac isomer by 1-H nmr spectroscopy. The photoluminescence spectrum is shown in FIG. 5, with a FWHM of 60 nm.

Synthesis Example 4

This example illustrates the preparation of Compound 16.

Example 4A

Preparation of 1-[2,6-dimethyl)phenyl]-2-(phenyl)-1H-benzimidazole (Intermediate Ligand 11)

50 g of 2,6-dimethylaniline was mixed with 47 g 2-fluoronitrobenzene and 30 g potassium fluoride and heated to 180° C. under nitrogen for 48 hrs in the absence of any solvent. The resulting material was cooled and purified by washing with cold methanol. 26.2 g (26%) intermediate secondary amine material was isolated with 99.9% purity as judged by UPLC.

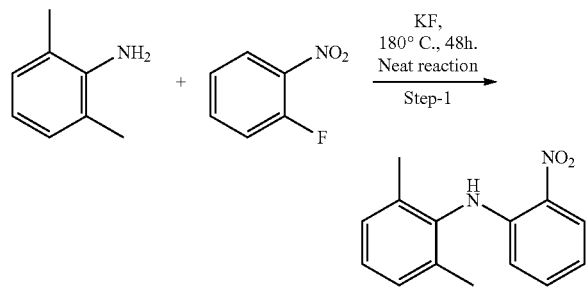

26 g of the secondary amine intermediate was mixed with 14.8 g benzaldehyde and 3 eq Na$_2$S$_2$O$_4$ in 0.5 L 50/50 ethanol/water and refluxed under nitrogen for 16 hrs. The product ligand (11) was isolated by column chromatography using 60-120 silica eluted gradually with 10% EtOAc+ Hexane to yield 13.6 g (42%) having ~99.8% purity by UPLC.

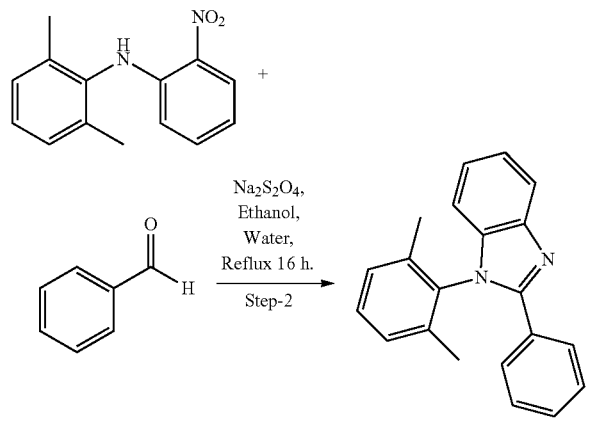

Example 4B

Preparation of Final Iridium Complex (Compound 16)

Ligand 11 from example 4A above was cyclometallated onto iridium in the same procedure as described in example 1C above. The Compound 16 material was identified as the tris cyclometallated fac isomer by 1-H nmr spectroscopy.

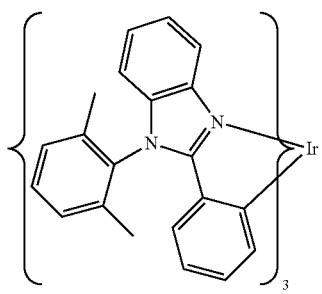

Cmpd 16

Comparative Synthesis Example A

This example illustrates the synthesis of Comparative Compound A.

Preparation of Ligand for Comparative Compound A 1-phenyl,2-(3-bromophenyl)-benzimidazole (12.0 g, 0.0344 mol),), 4-biphenylboronic acid (8.1 g, 0.0409 mol), 54 mL water, 240 mL monoglyme and potassium carbonate (14.4 g, 0.0142 mol) were sparged with nitrogen for 40 minutes. Tetrakistriphenylphosphine Pd(0) (2.0 g, 1.73 mmol) was quickly added and the mixture heated to 93° C. overnight. After cooling, the mixture was concentrated and taken up in DCM for water partitioning. The DCM solution was pre-absorbed to 78 g of neutral-alumina and then applied to a silica column for chromatography. The column was eluted with DCM followed by DCM with 2% methanol. Concentrated product cuts were combined and then methanol added to make a white slurry and filtered and dried to 12.3 g of white solid. 84% yield.

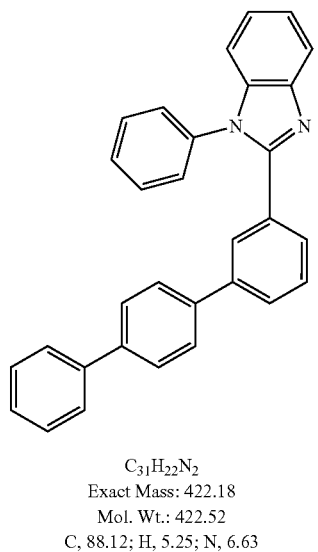 [SMILES: c1ccc(-c2ccc(-c3cccc(-c4nc5ccccc5n4-c4ccccc4)c3)cc2)cc1]

C$_{31}$H$_{22}$N$_2$
Exact Mass: 422.18
Mol. Wt.: 422.52
C, 88.12; H, 5.25; N, 6.63

Preparation of Comparative Compound A.

Take 4.5 g ligand from above, and 1.8 g iridium chloride in 20 mL 2-ethoxyethanol, and 2 mL water. Reflux this mixture under nitrogen for 72 hrs. The slurry turns dark yellow brown on reaching reflux—mostly clear initially but shortly after reflux starts a crystalline yellow ppt forms and densifies. The reaction progress was monitored by TLC then cooled to isolate material from the thick dark yellow slurry. The solvent was evaporated to dryness and the resulting dark orange brown solid was dissolved into methylene chloride and filtered through a fine frit with celite.

The deep yellow brown solution was added to 1.8 g silver triflate and ~10% methanol (ppts but quickly redissolves) and then stirred at 45° C. for 4 hrs.

Cool, then evaporate to dryness and extract into methylene chloride/methanol and filter through a fine frit with celite to remove silver salts. Evaporated this solution to dryness and redissolved into 2-ethoxyethanol and add 3.9 g more ligand and reflux this solution overnight.

Figure 6:
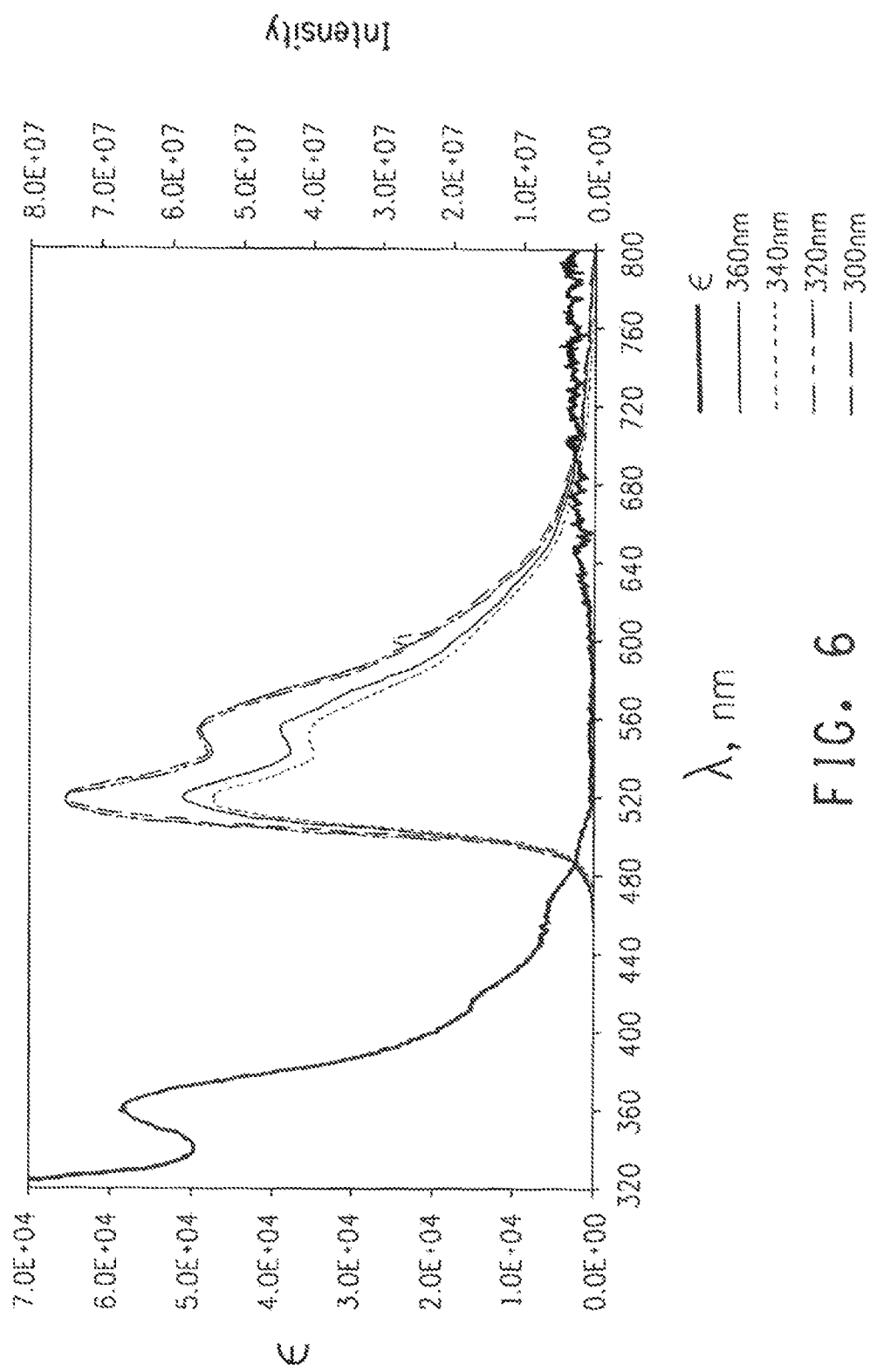
FIG. 6 includes emission spectra for Comparative Compound A.

The solution has much solid at this point and is green luminescent. Filter and dissolve the recovered solid into DCM and run through a stacked column of basic-alumina/acidic-alumina/florisil to elute a yellow orange solution and leave silver salts on top of column. Collect the eluent solution and evaporate to dryness. Redissolved into toluene and ran through basic-alumina/acidic-alumina eluted with toluene. Collect the yellow eluent (leaving orange brown color on top of column) and evaporated down and then add heptane to collect a yellow solid (3.2 g) and send for nmr in DCM which confirms the expected structure as a fac isomer of tris cyclometallate. The photoluminescence spectrum is shown in FIG. 6, with a FWHM of 77 nm.

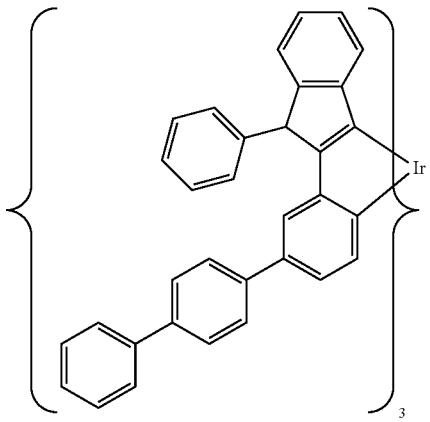

Comparative Compound A

Photoluminescence spectral data for the synthesized materials are reported in Table 1.

TABLE 1

Compound Photoluminescence Spectral Results

| Compound Designation | λ, nm | FWHM, nm |
| --- | --- | --- |
| Compound 1 | 508 | 56 |
| Compound 2 | 510 | 56 |
| Compound 3 | 513 | 60 |
| Compound 16 | 504 | 64 |
| Comparative Compound A | 520 | 77 |

Device Examples

The following device structure demonstrates the fabrication of OLED devices of Examples 1-3, and comparative example A.
(1) Materials
HIJ-1 is an electrically conductive polymer doped with a polymeric fluorinated sulfonic acid.
HT-1 is a fluorene-triarylamine polymer.
HT-2 is a triarylamine polymer.
Host-1 is a substituted indolocarbazole.
Host-2 is a substituted indolocarbazole that includes deuterium.
ET-1 is a fluoranthene derivative.
EIJ-1 is a quinolate compound.
The devices had the following structure on a glass substrate:
  anode=ITO (50 nm)
  hole injection layer=HIJ-1 (discussed below)
  hole transport layer=HT-1 (2 nm)
  hole transport layer=HT-2 (discussed below)
  photoactive layer, discussed below=Host-1:Host-2:dopant (60 nm), 50:41:9
  electron transport layer=ET-1 (discussed below)
  electron injection layer/cathode=EIJ-1/Al (3/100 nm)

The following device structure demonstrates the fabrication of OLED devices of of Examples 4, and comparative example B.
(1) Materials
HIJ-1 is an electrically conductive polymer doped with a polymeric fluorinated sulfonic acid.
HT-1 is a triarylamine molecule, TAPC
Host-1 is a substituted indolocarbazole that includes deuterium.
ET-1 is a organometallic compound, ZrQ.
EIJ-1 is CsF
The devices had the following structure on a glass substrate:
  anode=ITO (80 nm)
  hole injection layer=HIJ-1 (40 nm)
  hole transport layer=HT-1 (20 nm)
  photoactive layer=Host-1:dopant (60 nm), 80:20
  electron transport layer=ET-1 (10 nm)
  electron injection layer/cathode=EIJ-1/Al (1/100 nm)
(2) Device Fabrication OLED devices were fabricated by a combination of solution processing and thermal evaporation techniques. Patterned indium tin oxide (ITO) coated glass substrates from Thin Film Devices, Inc were used. These ITO substrates are based on Corning 1737 glass coated with ITO having a sheet resistance of 30 ohms/square and 80% light transmission. The patterned ITO substrates were cleaned ultrasonically in aqueous detergent solution and rinsed with distilled water. The patterned ITO was subsequently cleaned ultrasonically in acetone, rinsed with isopropanol, and dried in a stream of nitrogen.

Immediately before device fabrication the cleaned, patterned ITO substrates were treated with UV ozone for 10 minutes. Immediately after cooling, an aqueous dispersion of HIJ-1 was spin-coated over the ITO surface and heated to remove solvent. After cooling, the substrates were then spin-coated with a solution of HT-1, and then heated to remove solvent. After cooling the substrates were spin-coated with a solution of the photoactive layer materials in methyl benzoate and heated to remove solvent. Alternatively, HT-1 and emissive layer were deposited by vacuum thermal deposition in Example 4 and comparative example B. The substrates were masked and placed in a vacuum chamber. The electron transport layer was deposited by thermal evaporation, followed by a layer of CsF. Masks were then changed in vacuo and a layer of Al was deposited by thermal evaporation. The chamber was vented, and the devices were encapsulated using a glass lid, desiccant, and UV curable epoxy.
(3) Device Characterization The OLED samples were characterized by measuring their (1) current-voltage (I-V) curves, (2) electroluminescence radiance versus voltage, and (3) electroluminescence spectra versus voltage. All three measurements were performed at the same time and controlled by a computer. The current efficiency of the device at a certain voltage is determined by dividing the electroluminescence radiance of the LED by the current density needed to run the device. The unit is a cd/A. The color coordinates were determined using either a Minolta CS-100 meter or a Photoresearch PR-705 meter.

Examples 1 and 2 & Comparative Example A

These examples illustrate the use of compounds having Formula I as the light emitting material in a device.

The thickness of the hole injection layer was 220 nm. The thickness of the second hole transport layer was 20 nm. In Example 1, the dopant was Compound 1; in Example 2, the dopant was Compound 2; in Comparative Example A, the dopant was Comparative Compound A.

The results are given in Table 2 below.

TABLE 2

Device results

| Example | Dopant | CE (cd/A) | EQE (%) | Voltage @ 20 mA/cm2 (V) | CIE(x, y) | T70, hrs | FWHM (nm) | Current Density (mA/cm$^2$) |
|---|---|---|---|---|---|---|---|---|
| 1 | Compound 1 | 56.4 | 16.4 | 5.4 | 0.268 0.651 | 259 | 28.8 | 8.5 |
| 2 | Compound 2 | 60.5 | 17.5 | 5.6 | 0.265 0.655 | 302 | 26.7 | 7.8 |
| Comparative A | Comparative Compound A | 63.8 | 17.9 | 5.1 | 0.323 0.630 | 340 | 56.0 | 8.0 |

All data @ 2400 nits. CE is the current efficiency; EQE is the external quantum efficiency; CIE(x,y) are the x and y color coordinates according to the C.I.E. chromaticity scale (Commission Internationale de L'Eclairage, 1931); T70 is the time, in hours, to reach 70% of the initial luminance at the current density given and 50° C.

It can be seen from Tables 1 and 2 that the FWHM is significantly reduced when compounds of Formula I are present as the dopant, so the corresponding devices exhibit a more saturated green color. Other device operating parameters remain consistent with those expected for this configuration.

Example 3

These examples illustrate the use of Compound 3 as the light emitting material in a device.

The thickness of the hole injection layer was 100 nm. The thickness of the second hole transport layer was 140 nm. In Example 3, the dopant was Compound 3. Device operating measurements were made analogously to those reported in Table 2. For this configuration, CE=71.3 cd/A, EQE=19.0%, Voltage @ 20 mA/cm$^2$=5.8V, CIE(x,y)=(0.270,0.671), T70=238 hrs (current density=6.6 mA/cm$^2$), FWHM=39.9 nm.

Examples 4 & Comparative Example B

The results are given in Table 3 below.

TABLE 3

Device results

| Example | Dopant | CE (cd/A) | EQE (%) | Voltage @ 20 mA/cm2 (V) | CIE(x, y) | FWHM (nm) |
|---|---|---|---|---|---|---|
| 4 | Compound 16 | 64 | 18.8 | 4.7 | (0.3, 0.627) | 60 |
| Comparative B | Comparative Compound A | 29.6 | 8.1 | 8 | (0.321, 0.641) | 61.2 |

All data at 2000 nits. CE is the current efficiency; EQE is the external quantum efficiency; CIE(x,y) are the x and y color coordinates according to the C.I.E. chromaticity scale (Commission Internationale de L'Eclairage, 1931).

It can be seen from Table 1 that the FWHM of photoluminance band is significantly reduced with compounds 16, compared to comparative compound A. It can also been seen from Table 3 that device made from compound 16 as the emissive dopant gives higher EQE, lower voltage and narrower FWHM compared to comparative example B.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodi-

What is claimed is:

1. A compound having Formula I

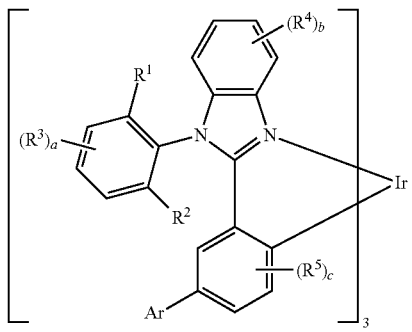

Formula I wherein:
- Ar is aryl or deuterated aryl;
- $R^1$ and $R^2$ are the same or different and are selected from the group consisting of alkyl, silyl, aryl, deuterated alkyl, deuterated silyl, and deuterated aryl;
- $R^3$-$R^5$ are the same or different at each occurrence and are selected from the group consisting of D, alkyl, silyl, aryl, deuterated alkyl, deuterated aryl, and deuterated silyl; where two adjacent $R^4$ groups can be joined together to form a fused 6-membered aromatic or deuterated aromatic ring;
- a and c are independently an integer from 0-3;
- b is an integer from 0-4; and
- the compound of Formula I emits light via photoluminescence using an exciting wavelength ranging from 300 to 360 nm, the emitted light having an emission profile over a range of wavelength, the full width at half the maximum intensity (FWHM) of the emission profile is less than or equal to 60 nm.

2. The compound of claim 1, wherein the compound exists as the isomer selected from the group consisting of fac structural isomer, mer structural isomer, and mixtures thereof.

3. The compound of claim 1, wherein Ar is selected from the group consisting of phenyl, 3-biphenyl, 4-biphenyl, 4,4'-terphenyl, 4,3'-terphenhyl, 3,4'-terphenyl, 3,3'-terphenyl, 3,5-terphenyl, 1-naphthyl, 2-naphthyl, 4-(1-naphthyl)phenyl, 4-(2-naphthyl)phenyl, 3-(1-naphthyl)phenyl, 3-(2-naphthyl)phenyl, substituted phenyl, substituted 3-biphenyl, substituted 4-biphenyl, substituted 4,4'-terphenyl, substituted 4,3'-terphenyl, substituted 3,4'-terphenyl, substituted 3,3'-terphenyl, substituted 3,5'-terphenyl, substituted 1-naphthyl, substituted 2-naphthyl, substituted 4-(1-naphthyl)phenyl, substituted 4-(2-naphthyl)phenyl, substituted 3-(1-naphthyl)phenyl, substituted 3-(2-naphthyl)phenyl, and deuterated analogs thereof.

4. The compound of claim 1, wherein $R^1$ and $R^2$ are independently selected from the group consisting of linear alkyl having 1-10 carbons, branched alkyl having 3-10 carbons, cycloalkyl having 6-10 ring carbons, silyl and deuterated analogs thereof.

5. The compound of claim 1, wherein $R^1$ and $R^2$ are independently selected from the group consisting of phenyl, naphthyl, biphenyl, terphenyl, substituted derivatives thereof, and deuterated analogs thereof.

6. The compound of claim 1, wherein a=b=c=0.

7. The compound of claim 1, wherein a>0 and $R^3$ is selected from the group consisting of D, alkyl having 1-10 carbons, and deuterated alkyl having 1-10 carbons.

8. The compound of claim 1, wherein b>0 and $R^4$ is selected from the group consisting of D, alkyl having 1-10 carbons, and deuterated alkyl having 1-10 carbons.

9. The compound of claim 1, wherein c>0 and $R^5$ is selected from the group consisting of D, alkyl having 1-10 carbons, and deuterated alkyl having 1-10 carbons.

10. The compound of claim 1, wherein the compound of Formula I is represented by Formula II

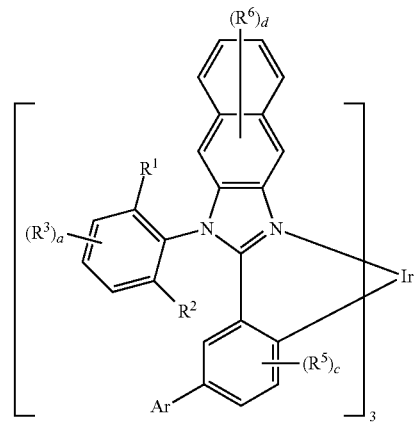

Formula II wherein
- Ar is aryl or deuterated aryl;
- $R^1$ and $R^2$ are the same or different and are selected from the group consisting of alkyl, silyl, aryl, deuterated alkyl, deuterated silyl, and deuterated aryl;
- $R^3$, $R^5$ and $R^6$ are the same or different at each occurrence and are selected from the group consisting of D, alkyl, silyl, aryl, deuterated alkyl, deuterated aryl, and deuterated silyl;
- a and c are independently an integer from 0-3; and
- d is an integer from 0-6.

11. The compound of claim 10, wherein the compound exists as the isomer selected from the group consisting of fac structural isomer, mer structural isomer, and mixtures thereof.

12. The compound of claim 1, wherein the compound is selected from compound 1 through compound 15

Compound 1
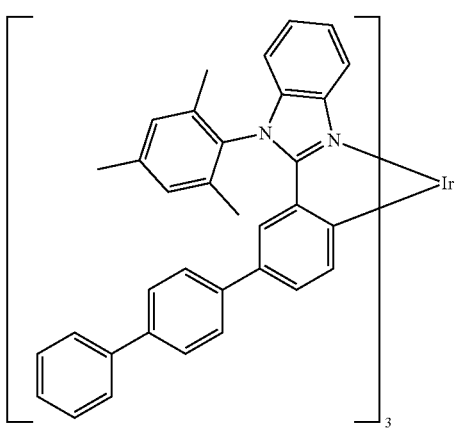
Compound 2
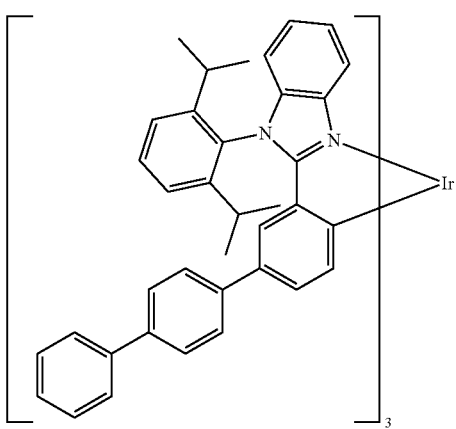
Compound 3
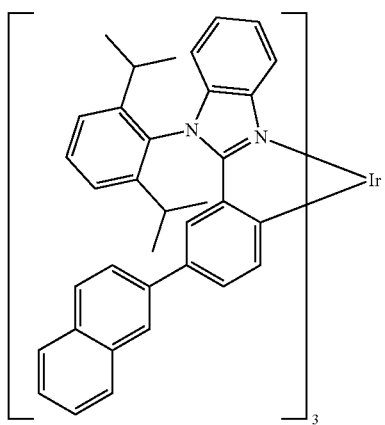
Compound 4
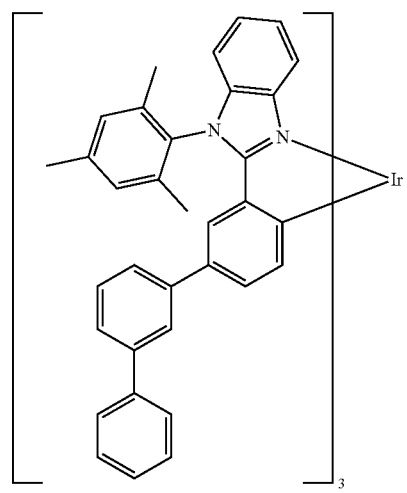
Compound 5
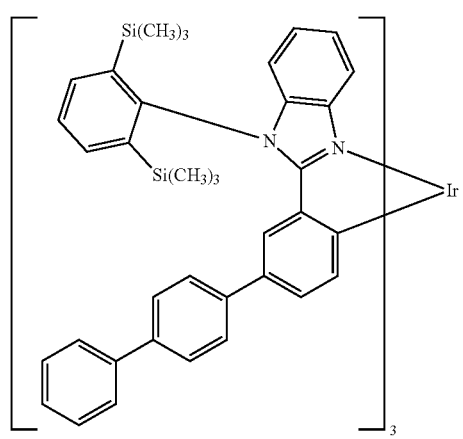
Compound 6
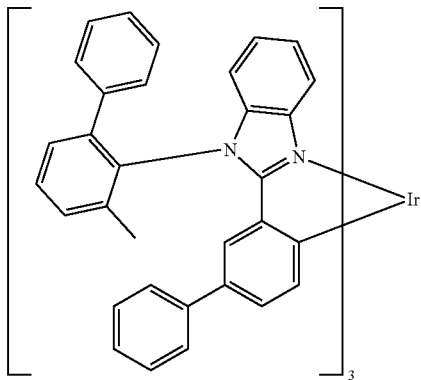

Compound 7
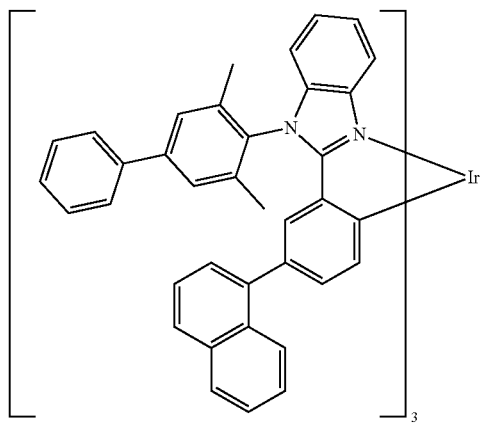
Compound 8
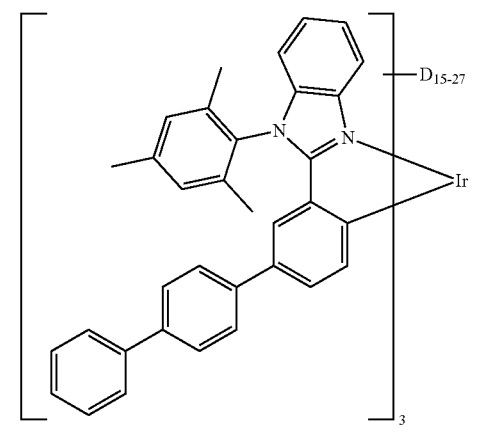
Compound 9
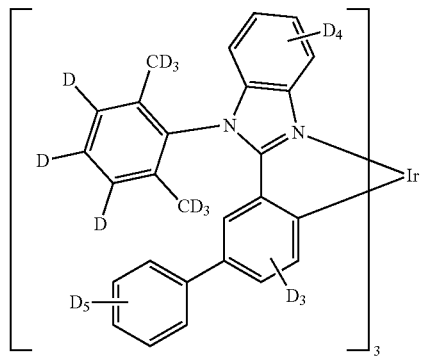
Compound 10
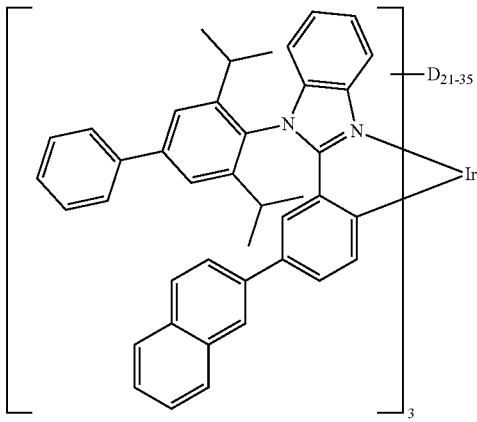
Compound 11
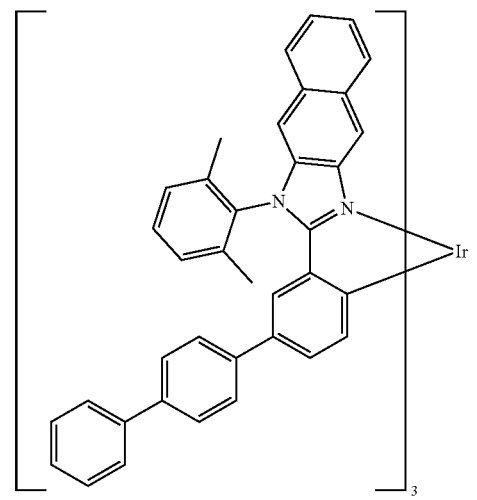
Compound 12
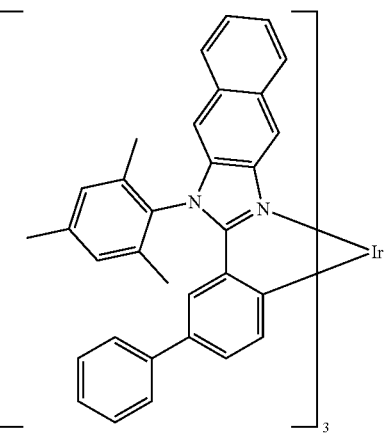

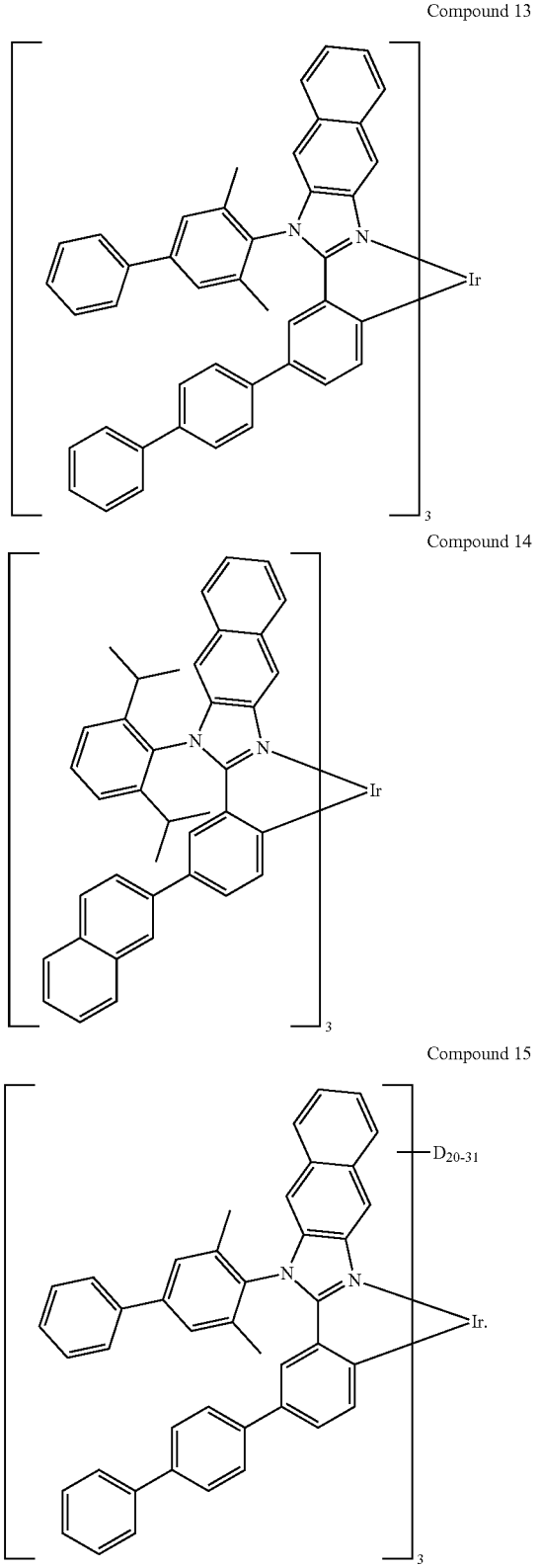

Compound 13

Compound 14

Compound 15

13. An organic electronic device comprising a first electrical contact, a second electrical contact and a photoactive layer therebetween, the photoactive layer comprising a compound having Formula I

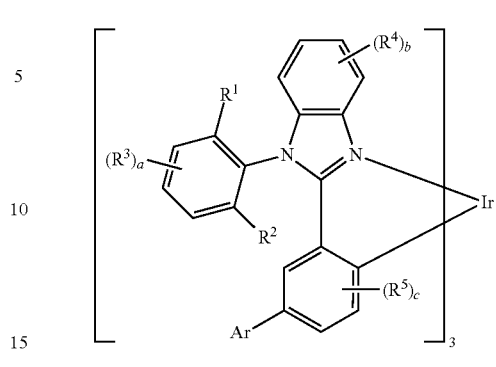

Formula I wherein:
Ar is aryl or deuterated aryl;
$R^1$ and $R^2$ are the same or different and are selected from the group consisting of alkyl, silyl, aryl, deuterated alkyl, deuterated silyl, and deuterated aryl;
$R^3$-$R^5$ are the same or different at each occurrence and are selected from the group consisting of D, alkyl, silyl, aryl, deuterated alkyl, deuterated aryl, and deuterated silyl; where two adjacent $R^4$ groups can be joined together to form a fused 6-membered aromatic or deuterated aromatic ring;
a and c are independently an integer from 0-3; and
b is an integer from 0-4; and
the compound of Formula I emits light via photoluminescence using an exciting wavelength ranging from 300 to 360 nm, the emitted light having an emission profile over a range of wavelength, the full width at half the maximum intensity (FWHM) of the emission profile is less than or equal to 60 nm.

14. The device of claim 13, wherein the photoactive layer comprises the compound of Formula I and further comprises a host material.

15. The device of claim 13, wherein the photoactive layer comprises a luminescent compound, a host material, and a compound having Formula I as a hole-trap material or an electron-trap material.

16. The device of claim 13, wherein the compound of Formula I is represented by Formula II

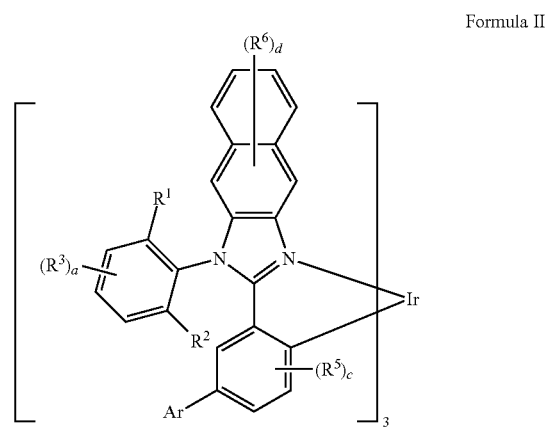

Formula II wherein:
- Ar is aryl or deuterated aryl;
- $R^1$ and $R^2$ are the same or different and are selected from the group consisting of alkyl, silyl, aryl, deuterated alkyl, deuterated silyl, and deuterated aryl;
- $R^3$, $R^5$, and $R^6$ are the same or different at each occurrence and is selected from the group consisting of D, alkyl, silyl, aryl, deuterated alkyl, deuterated aryl, and deuterated silyl;
- a and c are independently an integer from 0-3; and
- d is an integer from 0-6.

17. The device of claim 16, wherein the photoactive layer comprises the compound of Formula II and further comprises a host material.

18. The device of claim 16, wherein the photoactive layer comprises a luminescent compound, a host material, and a compound having Formula II as a hole-trap material or an electron-trap material.

* * * * *